(12) United States Patent
Studer et al.

(10) Patent No.: US 11,542,470 B2
(45) Date of Patent: Jan. 3, 2023

(54) METHODS OF DIFFERENTIATING STEM CELL-DERIVED PROPRIOCEPTORS

(71) Applicant: MEMORIAL SLOAN-KETTERING CANCER CENTER, New York, NY (US)

(72) Inventors: Lorenz Studer, New York, NY (US); Nadja Zeltner, Weehawken, NJ (US)

(73) Assignee: MEMORIAL SLOAN-KETTERING CANCER CENTER, New York, NY (US)

(*) Notice: Subject to any disclaimer, the term of this patent is extended or adjusted under 35 U.S.C. 154(b) by 719 days.

(21) Appl. No.: 16/199,801

(22) Filed: Nov. 26, 2018

(65) Prior Publication Data

US 2019/0093074 A1 Mar. 28, 2019

Related U.S. Application Data

(63) Continuation of application No. PCT/US2017/034690, filed on May 26, 2017.

(60) Provisional application No. 62/342,370, filed on May 27, 2016.

(51) Int. Cl.
| | |
|---|---|
| *C12N 5/0793* | (2010.01) |
| *C12N 5/0775* | (2010.01) |
| *C12N 5/074* | (2010.01) |
| *A61P 25/28* | (2006.01) |
| *A61K 35/30* | (2015.01) |

(52) U.S. Cl.
CPC .............. *C12N 5/062* (2013.01); *A61K 35/30* (2013.01); *A61P 25/28* (2018.01); *C12N 5/0667* (2013.01); *C12N 5/0696* (2013.01); *C12N 2501/115* (2013.01); *C12N 2501/13* (2013.01); *C12N 2501/155* (2013.01); *C12N 2501/16* (2013.01); *C12N 2501/415* (2013.01); *C12N 2501/42* (2013.01); *C12N 2501/999* (2013.01); *C12N 2506/02* (2013.01); *C12N 2533/52* (2013.01); *C12N 2533/90* (2013.01)

(58) Field of Classification Search
CPC .............. C12N 5/062; C12N 2501/155; C12N 2501/16; C12N 2501/415
See application file for complete search history.

(56) References Cited

U.S. PATENT DOCUMENTS

| | | | |
|---|---|---|---|
| 9,453,198 B2 * | 9/2016 | Studer | A61P 25/02 |
| 2008/0268019 A1 | 10/2008 | Badylak et al. | |
| 2009/0123433 A1 | 5/2009 | Shroff | |
| 2010/0034785 A1 | 2/2010 | Pederson et al. | |
| 2011/0296542 A1 | 12/2011 | Wang et al. | |
| 2015/0159135 A1 | 6/2015 | Davis et al. | |
| 2018/0298326 A1 * | 10/2018 | Studer | C12N 5/0626 |

FOREIGN PATENT DOCUMENTS

| | | |
|---|---|---|
| CA | 2 800 500 A1 | 12/2011 |
| WO | WO 2011/149762 A2 | 12/2011 |
| WO | WO 2015/077648 A1 | 5/2015 |
| WO | WO 2016/012570 A1 | 1/2016 |

OTHER PUBLICATIONS

Stem Cells: Scientific Progress and Future Research Directions. Department of Health and Human Services. Jun. 2001. Chapter 4. pp. 23-42 (Year: 2001).*
Cruciat CM, Niehrs C. Secreted and transmembrane wnt inhibitors and activators. Cold Spring Harb Perspect Biol. 2013;5(3):a015081. Published Mar. 1, 2013. (Year: 2013).*
Chen YG, Meng AM. Negative regulation of TGF-beta signaling in development. Cell Res. Dec. 2004;14(6):441-9. (Year: 2004).*
Blank U, Karlsson S. The role of Smad signaling in hematopoiesis and translational hematology. Leukemia. Sep. 2011;25(9):1379-88. (Year: 2011).*
Chambers, S., Fasano, C., Papapetrou, E. et al. Highly efficient neural conversion of human ES and iPS cells by dual inhibition of SMAD signaling. Nat Biotechnol 27, 275-280 (2009). (Year: 2009).*
Schnerch A, Cerdan C, Bhatia M. Distinguishing between mouse and human pluripotent stem cell regulation: the best laid plans of mice and men. Stem Cells. Mar. 31, 2010;28(3):419-30. (Year: 2010).*
Aridgides D, Salvador R, PereiraPerrin M. Trypanosoma cruzi coaxes cardiac fibroblasts into preventing cardiomyocyte death by activating nerve growth factor receptor TrkA. PLoS One. 2013;8(2):e57450. (Year: 2013).*
Ito K, Inoue KI, Bae SC, Ito Y. Runx3 expression in gastrointestinal tract epithelium: resolving the controversy. Oncogene. Mar. 12, 2009;28(10):1379-84 (Year: 2009).*
Menendez L, Yatskievych TA, Antin PB, Dalton S. Wnt signaling and a Smad pathway blockade direct the differentiation of human pluripotent stem cells to multipotent neural crest cells. Proc Natl Acad Sci U S A. Nov. 29, 2011;108(48):19240-5. (Year: 2011).*
Murry CE, Keller G. Differentiation of embryonic stem cells to clinically relevant populations: lessons from embryonic development. Cell. Feb. 22, 2008;132(4):661-80. (Year: 2008).*
Shi Y, Kirwan P, Livesey FJ. Directed differentiation of human pluripotent stem cells to cerebral cortex neurons and neural networks. Nat Protoc. Oct. 2012;7(10):1836-46. (Year: 2012).*
Chatterjee I, Li F, Kohler EE, Rehman J, Malik AB, Wary KK. Induced Pluripotent Stem (iPS) Cell Culture Methods and Induction of Differentiation into Endothelial Cells. Methods Mol Biol. Jan. 2016;1357:311-27. (First online 2015-Springer) (Year: 2016).*

(Continued)

*Primary Examiner* — Teresa E Knight
(74) *Attorney, Agent, or Firm* — Baker Botts L.L.P.

(57) ABSTRACT

The presently disclosed subject matter provides for in vitro methods of inducing differentiation of stem cells (e.g., human stem cells) into proprioceptors, proprioceptors generated by such methods, and compositions comprising such proprioceptors. The presently disclosed subject matter also provides for uses of such proprioceptors for preventing and/or treating disorders of proprioceptor neurons and/or neurodegenerative disorders (e.g., Friedreich's Ataxia).

20 Claims, 5 Drawing Sheets

(56) References Cited

OTHER PUBLICATIONS

Yang L, Geng Z, Nickel T, Johnson C, Gao L, Dutton J, Hou C, Zhang J. Differentiation of Human Induced-Pluripotent Stem Cells into Smooth-Muscle Cells: Two Novel Protocols. PLoS One. Jan. 15, 2016;11(1):e0147155. (Year: 2016).*

Thesaurus.com "How to use the slash symbol." (2013). Retrieved from thesaurus.com/e/grammar/slash/ (Year: 2013).*

Bansal et al., "Specific Inhibitor of FGF Receptor Signaling: FGF-2-Mediated Effects on Proliferation, Differentiation, and MAPK Activation are Inhibited by PD 173074 in Oligodendrocyte-Lineage Cells," J. Neurosci Res 74:486-493 (2003).

Cadigan, et al., "Wnt signaling: complexity at the surface," J Cell Sci. 119(3):395-402 (2006).

Calder et al., "Retinoic Acid-Mediated Regulation of GLI3 Enables Efficient Motoneuron Derivation from Human ESCs in the Absence of Extrinsic SHH Activation," J Neurosci. 35(33):11462-11481 (2015).

Chambers et al., "Combined small-molecule inhibition accelerates developmental timing and converts human pluripotent stem cells into nociceptors," Nat Biotechnol 30(7):715-720 (2012).

Chen et al., "Chemically defined conditions for human iPSC derivation and culture," Nat Methods 8(5):424-429 (2011).

Cuny et al., "Structure-activity relationship study of bone morphogenetic protein (BMP) signaling inhibitors," Bioorg. Med. Chem. Lett. 18(15):4388-4392 (2008).

Doble et al., "GSK-3: tricks of the trade for a multi-tasking kinase," J Cell Sci. 116(7):1175-1186 (2003).

Greenwood et al., "Identification of dividing, determined sensory neuron precursors in the mammalian neural crest," Development 126:3545-3559 (1999).

International Search Report dated Aug. 25, 2017 in International Application No. PCT/US17/34690.

Kikuchi et al., "Multiplicity of the interactions of Wnt proteins and their receptors," Cell Signaling 19:659-671 (2007).

Ma et al., "NEUROGENIN1 and NEUROGENIN2 control two distinct waves of neurogenesis in developing dorsal root ganglia," Genes & Development 13:1717-1728 (1999).

Paterson et al., "Preclinical studies of fibroblast growth factor receptor 3 as a therapeutic target in multiple myeloma," Br. J. Haematol. 124:595-603 (2004).

Pavan et al., "Specification of neural crest into sensory neuron and melanocyte lineages," Dev Biol. 366:55-63 (2012).

Racila et al., "Transient expression of OCT4 is sufficient to allow human keratinocytes to change their differentiation pathway," Gene Therapy 18(3):294-303 (2011).

Sun et al., "Design, Synthesis and Evaluations of Substituted 3-[(3- or 4-carboxyethylpyrrol-2-yl)methylidenyl]indolin-2-ones as inhibitors of VEGF, FGF and PDGF Receptor Tyrosine Kinases," J. Med. Chem. 42:5120-5130 (1999).

Takahashi et al., "Induction of Pluripotent Stem Cells from Mouse Embryonic and Adult Fibroblast Cultures by Defined Factors," Cell 126:663-676 (2006).

Tanaka et al., "FGF-induced vesicular release of Sonic hedgehog and retinoic acid in leftward nodal flow is critical for left-right determination," Nature 435:172-177 (2005).

Yu et al., "BMP type I receptor inhibition reduces heterotopic ossification," Nat Med 14(12):1363-1369 (2008).

F. Marmigère et al., "Specification and connectivity of neuronal subtypes in the sensory lineage," Nature Reviews. Neuroscience, vol. 8, Feb. 2007, pp. 114-127, XP055646452.

E. Eberhardt et al., "Pattern of Functional TTX-Resistant Sodium Channels Reveals a Developmental Stage of Human iPSC- and ESC-Derived Nociceptors," Stem Cell Reports, vol. 5, Sep. 2015, pp. 305-313, XP055646461.

M. Denham et al., "Multipotent Caudal Neural Progenitors Derived from Human Pluripotent Stem Cells That Give Rise to Lineages of the Central Peripheral Nervous System: Multipotent Caudal Neural Progenitors," Stem Cells, vol. 33, May 2015, pp. 1759-1770, XP055486435.

Communication pursuant to Rules 70(2) and 70a(2) EPC dated Jan. 3, 2020 and Extended European Search Report dated Dec. 5, 2019 in EP Application No. 17803662.0.

* cited by examiner

METHODS OF DIFFERENTIATING STEM CELL-DERIVED PROPRIOCEPTORS

CROSS-REFERENCE TO RELATED APPLICATION

This application is a continuation of International Patent Application No. PCT/US17/34690 filed on May 26, 2017, which claims priority to U.S. Provisional Application No. 62/342,370 filed on May 27, 2016, the content of each of which is incorporated by reference in its entirety, and to each of which priority is claims.

INTRODUCTION

The presently disclosed subject matter relates to sensory neurons (e.g., peripheral sensory neurons) derived from stem cells (e.g., human stem cells) and uses thereof for cell-based treatment and drug discovery in neurodegenerative disorders.

BACKGROUND OF THE SUBJECT MATTER

Peripheral sensory neurons are the afferent nervous system cells that respond to external stimuli, and transmit the information to the central nervous system (Pavan et al., *Dev Biol.* (2012 Jun. 1); 366(1):55-63). Sensory neurons can be divided into the following categories based on the type of stimulus they are responsive to: mechanoreceptors that respond to mechanical touch; proprioceptors that respond to limb and muscle movement; and nociceptors that respond to pain (Pavan et al., 2012). Protocols have been established to derive nociceptors from human stem cells, e.g., International Patent Publication No. WO 2011/149762 and Chambers et al., *Nat Biotechnol* (2012); 30:715-720. However, methods to derive proprioceptors from stem cells (e.g., human stem cells) have not been developed in the field. Therefore, there remains a need for an in vitro method and protocol for generating proprioceptors directly from stem cells (e.g., human stem cells.)

SUMMARY OF THE SUBJECT MATTER

The presently disclosed subject matter relates to peripheral sensory neurons, especially proprioceptors, derived from stem cells (e.g., human stem cells), by in vitro differentiation.

In certain embodiments, the presently disclosed subject matter provides in vitro methods for inducing differentiation of stem cells (e.g., human stem cells). In certain embodiments, the in vitro method for inducing differentiation of stem cells comprises contacting a population of stem cells with an effective amount(s) of one or more inhibitor of transforming growth factor beta (TGFβ)/Activin-Nodal signaling ("TGFβ inhibitor") and contacting the cells with one or more activator of wingless (Wnt) signaling ("Wnt activator") to produce a population of differentiated cells that express one or more proprioceptor marker, wherein the initial contact of the cells with the one or more Wnt activator is within an about four day period beginning with the initial contact with the one or more TGFβ inhibitor. For clarity, contact with the one or more Wnt activator may be initiated on the same day as the one or more TGFβ inhibitor or one, or two, or three, or four days later. In certain embodiments, the cells are initially contacted with the one or more Wnt activator and the one or more TGFβ inhibitor within a 96 hour period. In certain embodiments, the method comprises contacting the cells with the one or more TGFβ inhibitor for at least about 12 days. In certain embodiments, the method comprises contacting the cells with the one or more TGFβ inhibitor for at least about 13 days.

In time periods set forth herein, if the cells are to be initially contacted with two or more agents on the same day (within the same 24 hour period), they may be contacted with the cells in any order unless specified herein to the contrary. For example, if two or more agents are added to culture medium for the cells on the same day (within the same 24 hour period), they may be added in any order unless specified herein to the contrary.

In certain embodiments, the method comprises initially contacting the cells with the one or more Wnt activator on the same day (within the same 24 hour period) as the initial contact of the cells with the one or more TGFβ inhibitor. In certain embodiments, the method comprises contacting the population of stem cells with the one or more TGFβ inhibitor and the one or more Wnt activator from day 0 through day 11. In certain embodiments, the method comprises contacting the cells with the one or more Wnt activator for at least about 12 days. In certain embodiments, the method comprises contacting the cells with the one or more TGFβ inhibitor and the one or more Wnt activator from day 0 through day 12. In certain embodiments, the method comprises contacting the cells with the one or more Wnt activator for at least about 13 days. In certain embodiments, the concentration of the one or more Wnt activator for contacting with the cells on the first two days (e.g., day 0 and day 1) is less than about 1.5 µM (e.g., about 1 µM), or less than about 1.0 µM (e.g., about 0.9 µM, about 0.8 µM, about 0.7 µM, about 0.6 µM, about 0.5 µM, about 0.4 µM, about 0.3 µM, or about 0.1 µM). In certain embodiments, the concentration of the one or more Wnt activator for contacting with the cells on the first two days (e.g., day 0 and day 1) is about 0.6 µM. In certain embodiments, the concentration of the one or more Wnt activator for contacting with the cells after the first two days (e.g., from day 2 through day 12) is from about 0.1 µM to about 2.5 µM. In certain embodiments, the cells are contacted with the one or more Wnt activator in a concentration of about 1.5 µM.

In certain embodiments, the method comprises contacting the stem cells with an effective amount(s) of one or more BMP for up to 2 days. In certain embodiments, the initial contact of the stem cells with the one or more BMP is on the same day (within the same 24 hour period) as the initial contact of the stem cells with the TGFβ inhibitor. In certain embodiments, the effective amount of the one or more BMP is up to about 2 ng/mL. In certain embodiments, the method comprises contacting the population of stem cells with the one or more TGFβ inhibitor and the one or more Wnt activator from day 0 through day 12, and contacting the stem cells with the one or more BMP from day 0 through day 1.

In certain embodiments, the method comprises initially contacting the cells with the one or more Wnt activator between about 1 day and 4 days from the initial contact of the stem cells with the one or more TGFβ inhibitor. In certain embodiments, the method comprises initially contacting the cells with the one or more Wnt activator about 2 days after the initial contact of the stem cells with the one or more TGFβ inhibitor. In certain embodiments, the method comprises contacting the population of stem cells with the one or more TGFβ inhibitor from day 0 through day 11, and contacting the cells with the one or more Wnt activator from day 2 through day 11. In certain embodiments, the method comprises contacting the population of stem cells with the one or more TGFβ inhibitor from day 0 through day 12, and contacting the cells with the one or more Wnt activator from day 2 through day 12. In certain embodiments, the method comprises contacting the cells with the one or more Wnt activator for at least about 10 days. In certain embodiments, the method comprises contacting the cells with the one or more Wnt activator for at least about 11 days. In certain embodiments, the cells are contacted with the one or more Wnt activator in a concentration of from about 0.1 µM to about 2.5 µM. In certain embodiments, the cells are contacted with the one or more Wnt activator in a concentration of about 1.5 µM.

In certain embodiments, the method comprises contacting the stem cells with an effective amount(s) of one or more inhibitor of SMAD signaling ("SMAD inhibitor"). In certain embodiments, the method comprises initially contacting the stem cells with the one or more TGFβ inhibitor on the same day (within the same 24 hour period) as the initial contact of the stem cells with the one or more SMAD inhibitor. In certain embodiments, the method comprises contacting the cells with the one or more TGFβ inhibitor and the one or more SMAD inhibitor for at least about 12 days. In certain embodiments, the method comprises contacting the population of stem cells with the one or more TGFβ inhibitor and the one or more SMAD inhibitor from day 0 through day 11, and contacting the cells with the one or more Wnt activator from day 2 through day 11.

In certain embodiments, the method further comprises contacting the cells with an effective amount(s) of one or more inhibitor of fibroblast growth factor receptor (FGFR) family signaling ("FGFR inhibitor"). In certain embodiments, the methods further comprises contacting the cells with an effective amount(s) of one or more inhibitor of Notch signaling ("Notch inhibitor"). In certain embodiments, the method comprises initially contacting the cells with the one or more Wnt activator on the same day (within the same 24 hour period) as the initial contact of the one or more FGFR inhibitor, and the one or more Notch inhibitor. In certain embodiments, the method comprises contacting the population of stem cells with the one or more TGFβ inhibitor and the one or more SMAD inhibitor from day 0 through day 11, and contacting the cells with the one or more Wnt activator, the one or more FGFR inhibitor and the one or more Notch inhibitor from day 2 through day 11. In certain embodiments, the method comprises initially contacting the cells with the one or more FGFR inhibitor and the one or more Notch inhibitor about 2 days from the initial contact of the cells with the one or more Wnt activator. In certain embodiments, the method comprises contacting the population of stem cells with the one or more TGFβ inhibitor and the one or more Wnt activator from day 0 through day 12, contacting the cells with the one or more BMP from day 0 through day 1, and contacting the cells with the one or more FGFR inhibitor and the one or more Notch inhibitor from day 2 through day 12.

In certain embodiments, the population of stem cells are differentiated into a population of differentiated cells that express one or more proprioceptor marker on or after about 12 days from the initial contact with the one or more TGFβ inhibitor.

The presently disclosed subject matter also provides a population of in vitro differentiated cells expressing one or more proprioceptor marker, wherein the differentiated cell population is derived from a population of stem cells (e.g., human stem cells) by the above-described method. The presently disclosed subject matter further provides compositions comprising such differentiated cell population.

In addition, the presently disclosed subject matter provides a composition comprising a population of in vitro differentiated cells, wherein at least about 70% (e.g., at least about 75%, at least about 80%, at least about 85%, at least about 90%, at least about 95%, at least about 99%, or at least about 99.5%) of the population of cells express one or more proprioceptor marker, and wherein less than about 15% (e.g., less than about 10%, less than about 5%, less than about 4%, less than about 3%, less than about 2%, less than about 1%, less than about 0.5%, or less than about 0.1%) of the population of cells express one or more marker selected from the group consisting of peripheral sensory neuron markers, nociceptor markers, mechanoreceptor markers, stem cell markers, central nervous system (CNS) markers, Cranial Neural Crest (CNC) markers, Melanocyte-competent Neural Crest (MNC) markers, neuronal cell markers, and mesenchymal precursor markers. In certain non-limiting embodiments, the proprioceptor marker is selected from the group consisting of TrkC, Runx3, CDHL1, ETV1, and ETV4, and combinations thereof.

In certain non-limiting embodiments, the proprioceptor markers are selected from the group consisting of TrkC, Runx3, CDHL1, ETV1, and ETV4.

In certain non-limiting embodiments, the peripheral sensory neuron markers are selected from the group consisting of Brn3A, peripherin, and ISL1.

In certain non-limiting embodiments, the nociceptor markers are selected from the group consisting of TrkA and RUNX1.

In certain non-limiting embodiments, the mechanoreceptor markers are selected from the group consisting of TrkB and RET.

In certain non-limiting embodiments, the stem cell markers are selected from the group consisting of OCT4, NANOG, SOX2, LIN28, SSEA4 and SSEA3.

In certain non-limiting embodiments, the CNS markers are selected from the group consisting of PAX6, NESTIN, Vimentin, FOXG1, SOX2, TBR1, TBR2 and SOX1.

In certain non-limiting embodiments, the CNC markers are selected from the group consisting of PAX6, NESTIN, Vimentin, FOXG1, SOX2, TBR1, TBR2 and SOX1.

In certain non-limiting embodiments, the MNC markers are selected from the group consisting of PAX6, NESTIN, Vimentin, FOXG1, SOX2, TBR1, TBR2 and SOX1.

In certain non-limiting embodiments, the neuronal cell markers are selected from the group consisting of TUJ1, MAP2, NFH, BRN3A, ISL1, TH, ASCL1, CHAT, PHOX2B, PHOX2A, TRKA, TRKB, TRKC, 5HT, GABA, NOS, SST, TH, CHAT, DBH, Substance P, VIP, NPY, GnRH, and CGRP.

In certain non-limiting embodiments, the mesenchymal precursor markers are selected from the group consisting of SMA, Vimentin, HLA-ABC, CD105, CD90 and CD73.

In certain non-limiting embodiments, the composition comprises a population of from about $1 \times 10^4$ to about $1 \times 10^{10}$ cells expressing said one or more proprioceptor marker.

In certain non-limiting embodiments, the composition comprises a population of from about $1 \times 10^5$ to about $1 \times 10^7$ cells expressing said one or more proprioceptor marker.

Furthermore, the presently disclosed subject matter provides kits for inducing differentiation of stem cells. In certain embodiments, the kit comprises (a) an effective amount(s) of one or more TGFβ inhibitor, and (b) one or more Wnt activator in a concentration of from about 0.1 µM to about 2.5 µM. In certain embodiments, the kit further comprises (c) instructions for inducing differentiation of a population of stem cells into a population of differentiated cells that express one or more proprioceptor marker. In certain embodiments, the instructions comprise initially contacting the cells with the one or more Wnt activator within an about 4 day period from the initial contact of the stem cells with the one or more TFGβ inhibitor. In certain embodiments, the kit further comprises (d) an effective amount(s) of one or more SMAD inhibitor. In certain embodiments, the kit further comprises (e) an effective amount(s) of one or more FGFR inhibitor. In certain embodiments, the kit further comprises (f) an effective amount(s) of one or more Notch inhibitor. In certain embodiments, the kit further comprises (g) an effective amount(s) of one or more BMP (e.g., up to about 2 ng/mL).

In certain embodiments, the one or more TGFβ inhibitor is a small molecule selected from the group consisting of SB431542, derivatives thereof, and mixtures thereof. In certain embodiments, the TGFβ inhibitor is SB431542.

In certain embodiments, the one or more Wnt activator lowers glycogen synthase kinase 3β (GSK3β) for activation of Wnt signaling. In certain embodiments, the one or more Wnt activator is a small molecule selected from the group consisting of CHIR99021, derivatives thereof, and mixtures thereof. In certain embodiments, the Wnt activator is CHIR99021.

In certain embodiments, the one or more SMAD inhibitor is a small molecule selected from the group consisting of LDN193189, derivatives thereof, and mixtures thereof. In certain embodiments, the SMAD inhibitor is LDN193189.

In certain embodiments, the one or more FGFR inhibitors is a small molecule selected from the group consisting of SU5402, derivatives thereof, and mixtures thereof. In certain embodiments, the FGFR inhibitors is SU5402.

In certain embodiments, the one or more Notch inhibitors is a small molecule selected from the group consisting of DAPT, derivatives thereof, and mixtures thereof. In certain embodiments, the Notch inhibitor is DAPT.

In certain embodiments, the one or more BMP is selected from the group consisting of BMP2, BMP4, BMP6, and BMP7. In certain embodiments, the one or more BMP is BMP4.

In certain embodiments, the one or more proprioceptor marker is selected from the group consisting of TrkC, Runx3, CDHL1, ETV1, and ETV4, and combinations thereof.

In certain embodiments, the stem cells are human stem cells. In certain embodiments, the stem cells are non-human stem cells, for example non-human primate stem cells, rodent stem cells, dog stem cells, cat stem cells, etc. In certain embodiments, the stem cells are pluripotent stem cells. In certain embodiments, the human stem cells are selected from the group consisting of human embryonic stem cells, and human induced pluripotent stem cells, epiblast stem cells, and F-class pluripotent stem cells.

The presently disclosed subject matter further provides for methods of preventing and/or treating a disorder of proprioceptor neurons and/or a neurodegenerative disease or disorder in a subject. In certain embodiments, the method comprises administering an effective amount of the differentiated cell population described herein or a composition comprising thereof to a subject suffering from a disorder of proprioceptor neurons and/or a neurodegenerative disease or disorder.

The presently disclosed subject matter further provides differentiated cell population described herein or a composition comprising thereof for preventing and/or treating a disorder of proprioceptor neurons and/or a neurodegenerative disease or disorder in a subject.

The presently disclosed subject matter further provides uses of the differentiated cell population described herein or a composition comprising thereof in the manufacture of a medicament for preventing and/or treating a disorder of proprioceptor neurons and/or a neurodegenerative disease or disorder.

In certain embodiments, the neurodegenerative disease or disorder is selected from the group consisting of is Friedreich's Ataxia, and Parkinson's disease.

A. In certain non-limiting embodiments, the presently disclosed subject matter provides an in vitro method for inducing differentiation of stem cells, comprising:

contacting a population of stem cells with an effective amount(s) of one or more inhibitor of TGFβ/Activin-Nodal signaling, and contacting the cells with one or more activator of Wnt signaling in a concentration of from about 0.1 μM to about 2.5 μM to produce a population of differentiated cells that express one or more proprioceptor marker, wherein the initial contact of the cells with the one or more activator of Wnt signaling is within an about four day period from the initial contact of the population of stem cells with the one or more inhibitor of TGFβ/Activin-Nodal signaling.

A1. The foregoing method of A, wherein the initial contact of the cells with the one or more activator of Wnt signaling is on the same day (within the same 24 hour period) as the initial contact of said population of stem cells with the one or more inhibitor of TGFβ/Activin-Nodal signaling.

A2. The foregoing method of A, comprising contacting the cells with an effective amount(s) of one or more Bone morphogenetic protein (BMP) for up to about 2 days.

A3. The foregoing method of A, wherein the initial contact of the population of stem cells with the one or more BMP is on the same day (within the same 24 hour period) as the initial contact of said population of stem cells with the one or more inhibitor of TGFβ/Activin-Nodal signaling.

A4. The foregoing method of A, wherein the effective amount(s) of the one or more BMP is up to about 2 ng/mL.

A5. The foregoing method of A, wherein the initial contact of the cells with the one or more activator of Wnt signaling is between about 1 day and about 4 days from the initial contact of the population of stem cells with the one or more inhibitor of TGFβ/Activin-Nodal signaling.

A6. The foregoing method of A, wherein the initial contact of the cells with the one or more activator of Wnt signaling is about 2 days from the initial contact of the population of stem cells with the one or more inhibitor of TGFβ/Activin-Nodal signaling.

A7. The foregoing method of A, comprising contacting the population of stem cells with the one or more inhibitor of TGFβ/Activin-Nodal signaling for at least about 12 days.

A8. The foregoing method of A, comprising contacting the population of stem cells with the one or more activator of Wnt signaling for at least about 10 days.

A9. The foregoing method of A, comprising contacting the population of stem cells with the one or more activator of Wnt signaling for at least about 12 days.

A10. The foregoing method of A, comprising contacting the cells with the one or more activator of Wnt signaling in a concentration of about 1.5 μM.

A11. The foregoing method of A, comprising contacting the cells with the one or more activator of Wnt signaling in a concentration of less than about 1.0 μM.

A12. The foregoing method of A, further comprising contacting the population of stem cells with an effective amount(s) of one or more inhibitor of SMAD signaling.

A13. The foregoing method of A, wherein the initial contact of the population of stem cells with the one or more inhibitor of SMAD signaling is on the same day as the initial contact of said population of the stem cells with the one or more inhibitor of TGFβ/Activin-Nodal signaling.

A14. The foregoing method of A, further comprising contacting the cells with an effective amount(s) of one or more inhibitor of FGFR family signaling.

A15. The foregoing method of A, further comprising contacting the cells with an effective amount(s) of one or more inhibitor of Notch signaling.

A16. The foregoing method of A, comprising contacting the population of stem cells with the one or more inhibitor of TGFβ/Activin-Nodal signaling and the one or more inhibitor of SMAD signaling from day 0 through day 11, and contacting the population of stem cells with the one or more activator of Wnt signaling, the one or more inhibitor of FGFR family signaling, and the one or more inhibitor of Notch signaling from day 2 through day 11.

A17. The foregoing method of A, comprising contacting the population of stem cells with the one or more inhibitor of TGFβ/Activin-Nodal signaling and the one or more activator of Wnt signaling from day 0 through day 12, contacting the population of stem cells with the one or more BMP from day 0 through day 1, and contacting the cells with the one or more inhibitor of FGFR family signaling and the one or more inhibitor of Notch signaling from day 2 through day 12.

A18. The foregoing method of A, wherein the one or more inhibitor of TGFβ/Activin-Nodal signaling is a small molecule selected from the group consisting of SB431542, derivatives thereof, and mixtures thereof.

A19. The foregoing method of A, wherein the one or more inhibitor of TGFβ/Activin-Nodal signaling is SB431542.

A20. The foregoing method of A, wherein the one or more activator of Wnt signaling lowers glycogen synthase kinase 3β (GSK3β) for activation of Wnt signaling.

A21. The foregoing method of A, wherein the one or more activator of Wnt signaling is a small molecule selected from the group consisting of CHIR99021, derivatives thereof, and mixtures thereof.

A22. The foregoing method of A, wherein the one or more activator of Wnt signaling is CHIR99021.

A23. The foregoing method of A, wherein the one or more inhibitor of SMAD signaling is a small molecule selected from the group consisting of LDN193189, derivatives thereof, and mixtures thereof.

A24. The foregoing method of A, wherein the one or more inhibitor of SMAD signaling is LDN193189.

A25. The foregoing method of A, wherein the one or more inhibitor of FGFR family signaling is a small molecule selected from the group consisting of SU5402, derivatives thereof, and mixtures thereof.

A26. The foregoing method of A, wherein the one or more inhibitor of FGFR family signaling is SU5402.

A27. The foregoing method of A, wherein the one or more inhibitor of Notch family signaling is a small molecule selected from the group consisting of DAPT, derivatives thereof, and mixtures thereof.

A28. The foregoing method of A, wherein the one or more inhibitor of Notch family signaling is DAPT.

A29. The foregoing method of A, wherein the derivative of DAPT is (N—[N-(3,5-difluorophenacetyl)-L-alanyl]-(S)-phenylglycine-4-(4-(8-biotinamido)octylamino)benzoyl)benzyl)methylamide).

A30. The foregoing method of A, wherein the stem cells are human stem cells.

A31. The foregoing method of A, wherein the human stem cells are selected from the group consisting of human embryonic stem cells, human induced pluripotent stem cells, epiblast stem cells, and F-class pluripotent stem cells.

A32. The foregoing method of A, wherein the one or more proprioceptor marker is selected from the group consisting of TrkC, Runx3, CDHL1, ETV1, and ETV4, and combinations thereof.

A33. The foregoing method of A, wherein the one or more BMP is selected from the group consisting of BMP2, BMP4, BMP6, and BMP7.

A34. The foregoing method of A, wherein the one or more BMP is BMP4.

B. In certain embodiments, the presently disclosed subject matter provides a population of in vitro differentiated cells expressing one or more proprioceptor marker, wherein the differentiated cell population is derived from a population of stem cells by a method comprising:

contacting a population of stem cells with an effective amount(s) of one or more inhibitor of TGFβ/Activin-Nodal signaling, and contacting the cells with one or more activator of Wnt signaling in a concentration of from about 0.1 μM to about 2.5 μM to produce a population of differentiated cells that express one or more proprioceptor marker, wherein the initial contact of the cells with the one or more activator of Wnt signaling is within an about four day period from the initial contact of the population of stem cells with the one or more inhibitor of TGFβ/Activin-Nodal signaling.

B1. The foregoing differentiated cell population of B, wherein the initial contact of the cells with the one or more activator of Wnt signaling is on the same day as the initial contact of the population of stem cells with the one or more inhibitor of TGFβ/Activin-Nodal signaling on the same day.

B2. The foregoing differentiated cell population of B, wherein the population of stem cells are contacted with an effective amount(s) of one or more BMP for up to about 2 days.

B3. The foregoing differentiated cell population of B, wherein the initial contact of the population of stem cells with the one or more BMP is on the same day (within the same 24 hour period) as the initial contact of said population of stem cells with the one or more inhibitor of TGFβ/Activin-Nodal signaling.

B4. The foregoing differentiated cell population of B, wherein the effective amount(s) of the one or more BMP is up to about 2 ng/mL.

B5. The foregoing differentiated cell population of B, wherein the initial contact of the cells with the one or more activator of Wnt signaling is between about 1 day and 4 days from the initial contact of the population of stem cells with the one or more inhibitor of TGFβ/Activin-Nodal signaling.

B6. The foregoing differentiated cell population of B, wherein the initial contact of the cells with the one or more activator of Wnt signaling is about 2 days from the initial contact of the population of stem cells with the one or more inhibitor of TGFβ/Activin-Nodal signaling.

B7. The foregoing differentiated cell population of B, wherein the cells are contacted with the one or more inhibitor of TGFβ/Activin-Nodal signaling for at least about 12 days.

B8. The foregoing differentiated cell population of B, wherein the cells are contacted with the one or more activator of Wnt signaling for at least about 10 days.

B9. The foregoing differentiated cell population of B, wherein the cells are contacted with the one or more activator of Wnt signaling for at least about 12 days.

B10. The foregoing differentiated cell population of B, wherein the cells are contacted with the one or more activator of Wnt signaling in a concentration of about 1.5 µM.

B11. The foregoing differentiated cell population of B, wherein the cells are contacted with the one or more activator of Wnt signaling in a concentration of less than about 1.0 µM.

B12. The foregoing differentiated cell population of B, wherein the cells are contacted with an effective amount(s) of one or more inhibitor of SMAD signaling.

B13. The foregoing differentiated cell population of B, wherein the initial contact of the cells with the one or more inhibitor of SMAD signaling is on the same day as the initial contact of the population of stem cells with the one or more inhibitor of TGFβ/Activin-Nodal signaling.

B14. The foregoing differentiated cell population of B, wherein the cells are further contacted with an effective amount(s) of one or more inhibitor of FGFR family signaling.

B15. The foregoing differentiated cell population of B, wherein the cells are further contacted with an effective amount(s) of one or more inhibitor of Notch signaling.

B16. The foregoing differentiated cell population of B, wherein the cells are contacted with the one or more inhibitor of TGFβ/Activin-Nodal signaling and the one or more inhibitor of SMAD signaling from day 0 through day 11, and the cells are contacted with the one or more activator of Wnt signaling, the one or more inhibitor of FGFR family signaling, and the one or more inhibitor of Notch signaling from day 2 through day 11.

B17. The foregoing differentiated cell population of B, wherein the cells are contacted with the one or more inhibitor of TGFβ/Activin-Nodal signaling and the one or more activator of Wnt signaling from day 0 through day 12, the cells are contacted with the one or more BMP from day 0 through day 1, and the cells are contacted with the one or more inhibitor of FGFR family signaling and the one or more inhibitor of Notch signaling from day 2 through day 12.

B18. The foregoing differentiated cell population of B, wherein the one or more inhibitor of TGFβ/Activin-Nodal signaling is a small molecule selected from the group consisting of SB431542, derivatives thereof, and mixtures thereof.

B19. The foregoing differentiated cell population of B, wherein the one or more inhibitor of TGFβ/Activin-Nodal signaling is SB431542.

B20. The foregoing differentiated cell population of B, wherein the one or more activator of Wnt signaling lowers GSK3β for activation of Wnt signaling.

B21. The foregoing differentiated cell population of B, wherein the one or more activator of Wnt signaling is a small molecule selected from the group consisting of CHIR99021, derivatives thereof, and mixtures thereof.

B22. The foregoing differentiated cell population of B, wherein the one or more activator of Wnt signaling is CHIR99021.

B23. The foregoing differentiated cell population of B, wherein the one or more inhibitor of SMAD signaling is a small molecule selected from the group consisting of LDN193189, derivatives thereof, and mixtures thereof.

B24. The foregoing differentiated cell population of B, wherein the one or more inhibitor of SMAD signaling is LDN193189.

B25. The foregoing differentiated cell population of B, wherein the one or more inhibitor of FGFR family signaling is a small molecule selected from the group consisting of SU5402, derivatives thereof, and mixtures thereof.

B26. The foregoing differentiated cell population of B, wherein the one or more inhibitor of FGFR family signaling is of SU5402.

B27. The foregoing differentiated cell population of B, wherein the one or more inhibitor of Notch family signaling is a small molecule selected from the group consisting of DAPT, derivatives thereof, and mixtures thereof.

B28. The foregoing differentiated cell population of B, wherein the one or more inhibitor of Notch family signaling is DAPT.

B29. The foregoing differentiated cell population of B, wherein the derivative of DAPT is (N—[N-(3,5-difluorophenacetyl)-L-alanyl]-(S)-phenylglycine-4-(4-(8-biotinamido)octylamino)benzoyl)benzyl)methylamide).

B30. The foregoing differentiated cell population of B, wherein the stem cells are human stem cells.

B31. The foregoing differentiated cell population of B, wherein the human stem cells are selected from the group consisting of human embryonic stem cells, human induced pluripotent stem cells, epiblast stem cells, and F-class pluripotent stem cells.

B32. The foregoing differentiated cell population of B, wherein the one or more proprioceptor marker is selected from the group consisting of TrkC, Runx3, CDHL1, ETV1, and ETV4, and combinations thereof.

B33. The foregoing differentiated cell population of B, wherein the one or more BMP is selected from the group consisting of BMP2, BMP4, BMP6, and BMP7.

B33. The foregoing differentiated cell population of B, wherein the one or more BMP is BMP4.

C. In certain non-limiting embodiments, the presently disclosed subject matter provides an in vitro method for inducing differentiation of stem cells, comprising: contacting a population of stem cells with an effective amount(s) of one or more inhibitor of TGFβ/Activin-Nodal signaling for at least about 12 days, and contacting the cells with one or more activator of Wnt signaling in a concentration of from about 0.1 µM to about 2.5 µM for at least about 10 days to produce a population of differentiated cells that express one or more proprioceptor marker.

C1. The foregoing method of C, wherein the initial contact of the cells with the one or more activator of Wnt signaling is within an about four day period from the initial contact of the population of stem cells with the one or more inhibitor of TGFβ/Activin-Nodal signaling.

C2. The foregoing method of C, wherein the initial contact of population of stem cells with the one or more inhibitor of TGFβ/Activin-Nodal signaling is on the same day (within the same 24 hour period) as the initial contact of said cells with the one or more activator of Wnt signaling.

C3. The foregoing method of C, wherein the initial contact of the cells with the one or more activator of Wnt signaling is between about 1 day and about 4 days from the initial contact of the population of stem cells with the one or more inhibitor of TGFβ/Activin-Nodal signaling.

C4. The foregoing method of C, wherein the initial contact of the cells with the one or more activator of Wnt signaling is about 2 days after the initial contact of the population of stem cells with the one or more inhibitor of TGFβ/Activin-Nodal signaling.

C5. The foregoing method of C, comprising contacting the population of stem cells with an effective amount(s) of one or more inhibitor of SMAD signaling.

C6. The foregoing method of C, wherein the initial contact of the population of stem cells with the one or more inhibitor of TGFβ/Activin-Nodal signaling is on the same day (within the same 24 hour period) as the initial contact of said population of stem cells with the one or more inhibitor of SMAD signaling.

C7. The foregoing method of C, comprising contacting the population of stem cells with an effective amount(s) of one or more BMP for up to about 2 days.

C8. The foregoing method of C, wherein the initial contact of the population of stem cells with the one or more inhibitor of TGFβ/Activin-Nodal signaling is on the same day (within the same 24 hour period) as the initial contact of said population of stem cells with the one or more BMP.

C9. The foregoing method of C, wherein the effective amount of the one or more BMP is up to about 2 ng/mL.

C10. The foregoing method of C, further comprising contacting the cells with an effective amount(s) of one or more inhibitor of FGFR family signaling.

C11. The foregoing method of C, further comprising contacting the cells with an effective amount(s) of one or more inhibitor of Notch signaling.

C12. The foregoing method of C, wherein the initial contact of the cells with the one or more activator of Wnt signaling is on the same day (within the same 24 hour period) as the initial contact of the cells with the one or more inhibitor of FGFR family signaling and the one or more inhibitor of Notch signaling, or the initial contact of the cells with the one or more inhibitor of FGFR family signaling and the one or more inhibitor of Notch signaling is about 2 days from the initial contact of the cells with the one or more activator of Wnt signaling.

C13. The foregoing method of C, comprising contacting the population of stem cells with the one or more inhibitor of TGFβ/Activin-Nodal signaling and the one or more inhibitor of SMAD signaling from day 0 through day 11, and contacting the population of stem cells with the one or more activator of Wnt signaling, the one or more inhibitor of FGFR family signaling, and the one or more inhibitor of Notch signaling from day 2 through day 11.

C13. The foregoing method of C, comprising contacting the population of stem cells with the one or more inhibitor of TGFβ/Activin-Nodal signaling and the one or more activator of Wnt signaling from day 0 through day 12, contacting the population of stem cells with the one or more BMP from day 0 through day 1, and contacting the cells with the one or more inhibitor of FGFR family signaling and the one or more inhibitor of Notch signaling from day 2 through day 12.

C14. The foregoing method of C, wherein the one or more inhibitor of TGFβ/Activin-Nodal signaling is a small molecule selected from the group consisting of SB431542, derivatives thereof, and mixtures thereof.

C15. The foregoing method of C, wherein the one or more inhibitor of TGFβ/Activin-Nodal signaling is SB431542.

C16. The foregoing method of C, wherein the one or more activator of Wnt signaling lowers glycogen synthase kinase 3β (GSK3β) for activation of Wnt signaling.

C17. The foregoing method of C, wherein the one or more activator of Wnt signaling is a small molecule selected from the group consisting of CHIR99021, derivatives thereof, and mixtures thereof.

C18. The foregoing method of C, wherein the one or more activator of Wnt signaling is CHIR99021.

C19. The foregoing method of C, wherein the one or more inhibitor of SMAD signaling is a small molecule selected from the group consisting of LDN193189, derivatives thereof, and mixtures thereof.

C20. The foregoing method of C, wherein the one or more inhibitor of SMAD signaling is LDN193189.

C21. The foregoing method of C, wherein the one or more inhibitor of FGFR family signaling is a small molecule selected from the group consisting of SU5402, derivatives thereof, and mixtures thereof.

C22. The foregoing method of C, wherein the one or more inhibitor of FGFR family signaling is SU5402.

C23. The foregoing method of C, wherein the one or more inhibitor of Notch family signaling is a small molecule selected from the group consisting of DAPT, derivatives thereof, and mixtures thereof.

C24. The foregoing method of C, wherein the one or more inhibitor of Notch family signaling is DAPT.

C25. The foregoing method of C, wherein the derivative of DAPT is (N—[N-(3,5-difluorophenacetyl)-L-alanyl]-(S)-phenylglycine-4-(4-(8-biotinamido)octylamino)benzoyl) benzyl)methylamide).

C26. The foregoing method of C, wherein the stem cells are human stem cells.

C27. The foregoing method of C, wherein the human stem cells are selected from the group consisting of human embryonic stem cells, human induced pluripotent stem cells, epiblast stem cells, and F-class pluripotent stem cells.

C28. The foregoing method of C, wherein the one or more proprioceptor marker is selected from the group consisting of TrkC, Runx3, CDHL1, ETV1, and ETV4, and combinations thereof.

C29. The foregoing method of C, comprising contacting the cells with the one or more activator of Wnt signaling in a concentration of about 1.5 µM.

C30. The foregoing method of C, comprising contacting the cells with the one or more activator of Wnt signaling in a concentration of less than about 1.0 µM.

C31. The foregoing method of C, wherein the one or more BMP is selected from the group consisting of BMP2, BMP4, BMP6, and BMP7.

C32. The foregoing method of C, wherein the one or more BMP is BMP4.

D. In certain embodiments, the presently disclosed subject matter provides a population of in vitro differentiated cells expressing one or more proprioceptor marker, wherein the differentiated cell population is derived from a population of stem cells by a method comprising:

contacting a population of stem cells with an effective amount(s) of one or more inhibitor of TGFβ/Activin-Nodal signaling for at least about 12 days, and contacting the cells with one or more activator of Wnt signaling in a concentration of from about 0.1 µM to about 2.5 µM for at least about 10 days to produce a population of differentiated cells that express one or more proprioceptor marker.

D1. The foregoing differentiated cell population of D, wherein the initial contact of the cells with the one or more activator of Wnt signaling is within an about four day period from the initial contact of the population of stem cells with the one or more inhibitor of TGFβ/Activin-Nodal signaling.

D2. The differentiated cell population of D, wherein the initial contact of population of stem cells with the one or more inhibitor of TGFβ/Activin-Nodal signaling is on the same day (within the same 24 hour period) as the initial contact of said cells with the one or more activator of Wnt signaling.

D3. The differentiated cell population of D, wherein the initial contact of the cells with the one or more activator of Wnt signaling is between about 1 day and about 4 days from the initial contact of the population of stem cells with the one or more inhibitor of TGFβ/Activin-Nodal signaling.

D4. The differentiated cell population of D, wherein the initial contact of the cells with the one or more activator of Wnt signaling is about 2 days after the initial contact of the population of stem cells with the one or more inhibitor of TGFβ/Activin-Nodal signaling.

D5. The differentiated cell population of D, wherein the population of stem cells are contacted with an effective amount(s) of one or more inhibitor of SMAD signaling.

D6. The differentiated cell population of D, wherein the initial contact of the population of stem cells with the one or more inhibitor of TGFβ/Activin-Nodal signaling is on the same day (within the same 24 hour period) as the initial contact of said population of stem cells with the one or more inhibitor of SMAD signaling.

D7. The differentiated cell population of D, wherein the population of stem cells are contacted with an effective amount(s) of one or more BMP for up to about 2 days.

D8. The differentiated cell population of D, wherein the initial contact of the population of stem cells with the one or more inhibitor of TGFβ/Activin-Nodal signaling is on the same day (within the same 24 hour period) as the initial contact of said population of stem cells with the one or more BMP.

D9. The differentiated cell population of D, wherein the effective amount of the one or more BMP is up to about 2 ng/mL.

D10. The foregoing differentiated cell population of D, wherein the cells are further contacted with an effective amount(s) one or more inhibitor of FGFR family signaling.

D11. The foregoing differentiated cell population of D, wherein the cells are further contacted with an effective amount(s) one or more inhibitor of Notch signaling.

D12. The foregoing differentiated cell population of D, wherein the initial contact of the cells with the one or more activator of Wnt signaling is on the same day as the initial contact of the one or more inhibitor of FGFR family signaling, and the one or more inhibitor of Notch signaling, or the initial contact of the cells with the one or more inhibitor of FGFR family signaling, and the one or more inhibitor of Notch signaling is about 2 days from the initial contact of the cells with the one or more activator of Wnt signaling.

D13. The foregoing differentiated cell population of D, wherein the population of stem cells are contacted with the one or more inhibitor of TGFβ/Activin-Nodal signaling and the one or more inhibitor of SMAD signaling from day 0 through day 11, and are contacted with the one or more activator of Wnt signaling, the one or more inhibitor of FGFR family signaling, and the one or more inhibitor of Notch signaling from day 2 through day 11.

D14. The foregoing differentiated cell population of D, wherein the population of stem cells are contacted with the one or more inhibitor of TGFβ/Activin-Nodal signaling and the one or more activator of Wnt signaling from day 0 through day 12, and the cells are contacted with the one or more inhibitor of FGFR family signaling and the one or more inhibitor of Notch signaling from day 2 through day 11.

D15. The foregoing differentiated cell population of D, wherein the one or more inhibitor of TGFβ/Activin-Nodal signaling is a small molecule selected from the group consisting of SB431542, derivatives thereof, and mixtures thereof.

D16. The foregoing differentiated cell population of D, wherein the one or more inhibitor of TGFβ/Activin-Nodal signaling is SB431542.

D17. The foregoing differentiated cell population of D, wherein the one or more inhibitor of SMAD signaling is a small molecule selected from the group consisting of LDN193189, derivatives thereof, and mixtures thereof.

D18. The foregoing differentiated cell population of D, wherein the one or more inhibitor of SMAD signaling is LDN193189.

D19. The foregoing differentiated cell population of D, wherein the one or more activator of Wnt signaling lowers GSK3β for activation of Wnt signaling.

D20. The foregoing differentiated cell population of D, wherein the one or more activator of Wnt signaling is a small molecule selected from the group consisting of CHIR99021, derivatives thereof, and mixtures thereof.

D21. The foregoing differentiated cell population of D, wherein the one or more activator of Wnt signaling is CHIR99021.

D22. The foregoing differentiated cell population of D, wherein the one or more inhibitor of FGFR family signaling is a small molecule selected from the group consisting of SU5402, derivatives thereof, and mixtures thereof.

D23. The foregoing differentiated cell population of D, wherein the one or more inhibitor of FGFR family signaling is of SU5402.

D24. The foregoing differentiated cell population of D, wherein the one or more inhibitor of Notch family signaling is a small molecule selected from the group consisting of DAPT, derivatives thereof, and mixtures thereof.

D25. The foregoing differentiated cell population of D, wherein the one or more inhibitor of Notch family signaling is DAPT.

D26. The foregoing differentiated cell population of D, wherein the derivative of DAPT is (N—[N-(3,5-difluorophenacetyl)-L-alanyl]-(8)-phenylglycine-4-(4-(8-biotinamido)octylamino)benzoyl)benzyl)methylamide).

D27. The foregoing differentiated cell population of D, wherein the stem cells are human stem cells.

D28. The foregoing differentiated cell population of D, wherein the human stem cells are selected from the group consisting of human embryonic stem cells, human induced pluripotent stem cells, epiblast stem cells, and F-class pluripotent stem cells.

D29. The foregoing differentiated cell population of D, wherein the one or more proprioceptor marker is selected from the group consisting of TrkC, Runx3, CDHL1, ETV1, and ETV4, and combinations thereof.

D30. The foregoing differentiated cell population of D, wherein the cells are contacted with the one or more activator of Wnt signaling in a concentration of about 1.5 μM. D31. The foregoing differentiated cell population of D, wherein the cells are contacted with the one or more activator of Wnt signaling in a concentration of less than about 1.0 μM.

D32. The foregoing differentiated cell population of D, wherein the one or more BMP is selected from the group consisting of BMP2, BMP4, BMP6, and BMP7.

D33. The foregoing differentiated cell population of D, wherein the one or more BMP is BMP4.

E. In certain embodiments, the presently disclosed subject matter provides a composition comprising the foregoing differentiated cell population.

F. In certain embodiments, the presently disclosed subject matter provides a method of preventing and/or treating a disorder of proprioceptor neurons and/or a neurodegenerative disease or disorder in a subject, comprising administering to a subject suffering from a disorder of proprioceptor neurons and/or a neurodegenerative disease or disorder an effective amount of one of the followings:

(a) the foregoing differentiated cell population; and
(b) a composition comprising the foregoing differentiated cell population.

F1. The foregoing method of F, wherein the neurodegenerative disease or disorder is Friedreich's Ataxia, and Parkinson's disease.

G. In certain embodiments, the presently disclosed subject matter provides the foregoing differentiated cell population for preventing and/or treating a disorder of proprioceptor neurons and/or a neurodegenerative disease or disorder in a subject.

G1. The foregoing differentiated cell population of G, wherein the neurodegenerative disease or disorder is Friedreich's Ataxia, and Parkinson's disease.

H. In certain embodiments, the presently disclosed subject matter provides a composition comprising the foregoing differentiated cell population for preventing and/or treating a disorder of proprioceptor neurons and/or a neurodegenerative disease or disorder in a subject.

H1. The foregoing differentiated cell population of H, wherein the neurodegenerative disease or disorder is Friedreich's Ataxia, and Parkinson's disease.

I. In certain embodiments, the presently disclosed subject matter provides use of the foregoing differentiated cell population in the manufacture of a medicament for preventing and/or treating a disorder of proprioceptor neurons and/or a neurodegenerative disease or disorder.

I1. The foregoing use of I, wherein the genetic neurodegenerative disease or disorder is Friedreich's Ataxia, and Parkinson's disease.

J. In certain embodiments, the presently disclosed subject matter provides use of a composition comprising the foregoing differentiated cell population in the manufacture of a medicament for preventing and/or treating a disorder of proprioceptor neurons and/or a neurodegenerative disease or disorder.

J1. The foregoing use of J, wherein the genetic neurodegenerative disease or disorder is Friedreich's Ataxia, and Parkinson's disease.

K. In certain embodiments, the presently disclosed subject matter provides for a kit for inducing differentiation of stem cells, comprising:

(a) an effective amount(s) of one or more inhibitor of TGFβ/Activin-Nodal signaling, and
(b) one or more activator of Wnt signaling in a concentration of from about 0.1 µM to about 2.5 µM.

K1. The foregoing kit of K, further comprising (c) instructions for inducing differentiation of the stem cells into a population of differentiated cells that express one or more proprioceptor marker, wherein the instructions comprise contacting a population of stem cells with the one or more inhibitor of TGFβ/Activin-Nodal signaling, and contacting the cells with the one or more activator of Wnt signaling, wherein the initial contact of the cells with the one or more activator of Wnt signaling is within an about four day period from the initial contact of the population of stem cells with the one or more inhibitor of TGFβ/Activin-Nodal signaling.

K1. The foregoing kit of K, further comprising an effective amount(s) of one or more Bone morphogenetic protein (BMP), wherein the instructions comprise contacting the population of the stem cells with the one or more BMP for up to about 2 days.

K2. The foregoing kit of K, wherein the instructions comprise initially contacting the population of stem cells with the one or more BMP on the same day (within the same 24 hour period) as the initial contact of said population of stem cells with the one or more inhibitor of TGFβ/Activin-Nodal signaling.

K3. The foregoing kit of K, wherein the effective amount(s) of the one or more BMP is up to about 2 ng/mL.

K4. The foregoing kit of K, wherein the instructions comprise initially contacting the cells with the one or more activator of Wnt signaling between about 1 day and about 4 days from the initial contact of the population of stem cells with the one or more inhibitor of TGFβ/Activin-Nodal signaling.

K5. The foregoing kit of K, wherein the instructions comprise initially contacting the cells with the one or more activator of Wnt signaling about 2 days from the initial contact of the population of stem cells with the one or more inhibitor of TGFβ/Activin-Nodal signaling.

K6. The foregoing kit of K, the instructions comprise contacting the population of stem cells with the one or more inhibitor of TGFβ/Activin-Nodal signaling for at least about 12 days.

K7. The foregoing kit of K, the instructions comprise contacting the population of stem cells with the one or more activator of Wnt signaling for at least about 10 days.

K8. The foregoing kit of K, the instructions comprise initially contacting the population of stem cells with the one or more activator of Wnt signaling for at least about 12 days.

K9. The foregoing kit of K, wherein the concentration of the one or more activator of Wnt signaling is about 1.5 µM.

K10. The foregoing kit of K, wherein the concentration of the one or more activator of Wnt signaling is less than about 1.0 µM.

K11. The foregoing kit of K, further comprising an effective amount(s) of one or more inhibitor of SMAD signaling K12. The foregoing kit of K, wherein the instructions comprise initially contacting the population of stem cells with the one or more inhibitor of TGFβ/Activin-Nodal signaling on the same day as the initial contact of the population of the stem cells with the one or more inhibitor of SMAD signaling.

K13. The foregoing kit of K, wherein the instructions comprise contacting the population of stem cells with the one or more inhibitor of TGFβ/Activin-Nodal signaling and the one or more inhibitor of SMAD signaling for at least about 12 days.

K14. The foregoing kit of K, further comprising an effective amount(s) of one or more inhibitor of FGFR family signaling.

K15. The foregoing kit of K, further comprising an effective amount(s) of one or more inhibitor of Notch family signaling.

K16. The foregoing kit of K, wherein the instructions comprise initially contacting the cells with the one or more activator of Wnt signaling on the same day as the initial contact of the cells with the one or more inhibitor of FGFR family signaling and the one or more inhibitor of Notch signaling, or the instructions comprise initially contacting the one or more inhibitor of FGFR family signaling and the one or more inhibitor of Notch signaling is about 2 days from the initial contact of the cells with the one or more activator of Wnt signaling.

K17. The foregoing kit of K, wherein the instructions comprise contacting the population of stem cells with the one or more inhibitor of TGFβ/Activin-Nodal signaling and the one or more inhibitor of SMAD signaling from day 0 through day 11, and contacting the population of stem cells with the one or more activator of Wnt signaling, the one or more inhibitor of FGFR family signaling, and the one or more inhibitor of Notch signaling from day 2 through day 11.

K18. The foregoing kit of K, wherein the instructions comprise contacting the population of stem cells with the one or more inhibitor of TGFβ/Activin-Nodal signaling and the one or more activator of Wnt signaling from day 0 through day 12, and contacting the cells with the one or more inhibitor of FGFR family signaling and the one or more inhibitor of Notch signaling from day 2 through day 12.

K19. The foregoing kit of K, wherein the one or more inhibitor of TGFβ/Activin-Nodal signaling is a small molecule selected from the group consisting of SB431542, derivatives thereof, and mixtures thereof.

K20. The foregoing kit of K, wherein the one or more inhibitor of TGFβ/Activin-Nodal signaling is SB431542.

K21. The foregoing kit of K, wherein the one or more inhibitor of SMAD signaling is a small molecule selected from the group consisting of LDN193189, derivatives thereof, and mixtures thereof.

K22. The foregoing kit of K, wherein the one or more inhibitor of SMAD signaling is LDN193189.

K23. The foregoing kit of K, wherein the one or more activator of Wnt signaling lowers GSK3β for activation of Wnt signaling.

K24. The foregoing kit of K, wherein the one or more activator of Wnt signaling is a small molecule selected from the group consisting of CHIR99021, derivatives thereof, and mixtures thereof.

K25. The foregoing kit of K, wherein the one or more activator of Wnt signaling is CHIR99021.

K26. The foregoing kit of K, wherein the one or more inhibitor of FGFR family signaling is a small molecule selected from the group consisting of SU5402, derivatives thereof, and mixtures thereof.

K27. The foregoing kit of K, wherein the one or more inhibitor of FGFR family signaling is SU5402.

K28. The foregoing kit of K, wherein the one or more inhibitor of Notch family signaling is a small molecule selected from the group consisting of DAPT, derivatives thereof, and mixtures thereof.

K29. The foregoing kit of K, wherein the one or more inhibitor of Notch family signaling is DAPT.

K30. The foregoing kit of K, wherein the derivative of DAPT is (N—[N-(3,5-difluorophenacetyl)-L-alanyl]-(S)-phenylglycine-4-(4-(8-biotinamido)octylamino)benzoyl)benzyl)methylamide).

K31. The foregoing kit of K, wherein the stem cells are human stem cells.

K32. The foregoing kit of K, wherein the human stem cells are selected from the group consisting of human embryonic stem cells, human induced pluripotent stem cells, epiblast stem cells, and F-class pluripotent stem cells.

K33. The foregoing kit of K, wherein the one or more proprioceptor marker is selected from the group consisting of TrkC, Runx3, CDHL1, ETV1, and ETV4, and combinations thereof.

K34. The foregoing kit of K, wherein the one or more BMP is selected from the group consisting of BMP2, BMP4, BMP6, and BMP7.

K35. The foregoing kit of K, wherein the one or more BMP is BMP4.

L. A composition comprising a population of in vitro differentiated cells, wherein at least about 70% (e.g., at least about 75%, at least about 80%, at least about 85%, at least about 90%, at least about 95%, at least about 99%, or at least about 99.5%) of the population of cells express one or more proprioceptor marker, and wherein less than about 15% (e.g., less than about 10%, less than about 5%, less than about 4%, less than about 3%, less than about 2%, less than about 1%, less than about 0.5%, or less than about 0.1%) of the population of cells express one or more marker selected from the group consisting of nociceptor markers, mechanoceptor markers, peripheral sensory neuron markers, stem cell markers, CNS markers, Cranial Neural Crest (CNC) markers, Melanocyte-competent Neural Crest (MNC) markers, neuronal cell markers, and mesenchymal precursor markers.

L1. The foregoing of the composition of L, wherein the proprioceptor markers are selected from the group consisting of TrkC, Runx3, CDHL1, ETV1, and ETV4.

L2. The foregoing of the composition of L, wherein the peripheral sensory neuron markers are selected from the group consisting of Brn3A, peripherin, and ISL1.

L3. The foregoing of the composition of L, wherein the nociceptor markers are selected from the group consisting of TrkA and RUNX1.

L4. The foregoing of the composition of L, wherein the mechanoreceptor markers are selected from the group consisting of TrkB and RET.

L5. The foregoing of the composition of L, wherein the stem cell markers are selected from the group consisting of OCT4, NANOG, SOX2, LIN28, SSEA4 and SSEA3.

L6. The foregoing of the composition of L, wherein the CNS markers are selected from the group consisting of PAX6, NESTIN, Vimentin, FOXG1, SOX2, TBR1, TBR2 and SOX1.

L7. The foregoing of the composition of L, wherein the CNC markers are selected from the group consisting of PAX6, NESTIN, Vimentin, FOXG1, SOX2, TBR1, TBR2 and SOX1.

L8. The foregoing of the composition of L, wherein the MNC markers are selected from the group consisting of PAX6, NESTIN, Vimentin, FOXG1, SOX2, TBR1, TBR2 and SOX1.

L9. The foregoing of the composition of L, wherein the neuronal cell markers are selected from the group consisting of TUJ1, MAP2, NFH, BRN3A, ISL1, TH, ASCL1, CHAT, PHOX2B, PHOX2A, TRKA, TRKB, TRKC, 5HT, GABA, NOS, SST, TH, CHAT, DBH, Substance P, VIP, NPY, GnRH, and CGRP.

L10. The foregoing of the composition of L, wherein the mesenchymal precursor markers are selected from the group consisting of SMA, Vimentin, HLA-ABC, CD105, CD90 and CD73.

L11. The foregoing of the composition of L, comprising a population of from about $1 \times 10^4$ to about $1 \times 10^{10}$ cells expressing said one or more proprioceptor marker.

J. A composition comprising a population of in vitro differentiated cells,
wherein at least about 10% of the population of cells express one or more proprioceptor marker, at least about 10% of the population of cells express one or more nociceptor marker, at least about 10% of the population of cells express one or more mechanoreceptor marker, and
wherein less than about 15% of the population of cells express one or more marker selected from the group consisting of peripheral sensory neuron markers, stem cell markers, central nervous system (CNS) markers, Cranial Neural Crest (CNC) markers, Melanocyte-competent Neural Crest (MNC) markers, neuronal cell markers, and mesenchymal precursor markers.

DETAILED DESCRIPTION OF THE SUBJECT MATTER

Figure 1A:
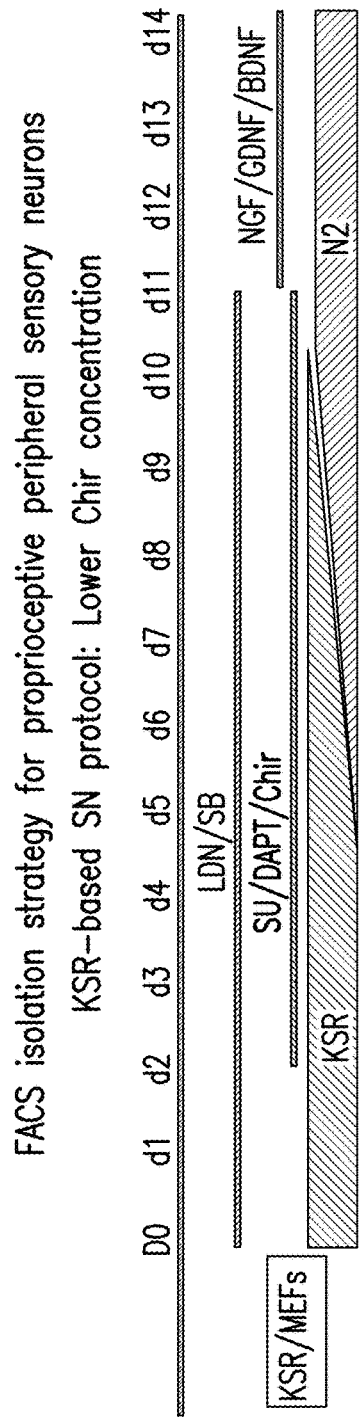
FIGS. 1A-1D. Induction of proprioceptors from human embryonic stem cells ("hESCs) by a KSR medium. (A) Schematic illustration of one cell culture medium for differentiation of hESCs to proprioceptors in accordance with one non-limiting embodiment of the presently disclosed subject matter. (B)-(D) Results of Flow Cytometry of cultured cells.

The presently disclosed subject matter relates to in vitro methods for inducing differentiation of stem cells (e.g., human stem cells) to sensory neurons, in particular, peripheral sensory neurons, e.g., proprioceptors (proprioceptive sensory neurons), and cells produced by such methods and compositions comprising such cells.

For purposes of clarity of disclosure and not by way of limitation, the detailed description is divided into the following subsections:

5.1. Definitions
5.2. Method of Differentiating Stem Cells
5.3 Composition Comprising Differentiated Cell Population
5.4. Method of Preventing and/or Treating Disorders;
5.5. Kits
5.1 Definitions The terms used in this specification generally have their ordinary meanings in the art, within the context of the subject matter and in the specific context where each term is used. Certain terms are discussed below, or elsewhere in the specification, to provide additional guidance to the practitioner in describing the compositions and methods of the subject matter and how to make and use them.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold, or within 2-fold, of a value.

As used herein, the term "signaling" in reference to a "signal transduction protein" refers to a protein that is activated or otherwise affected by ligand binding to a membrane receptor protein or some other stimulus. Examples of signal transduction protein include, but are not limited to, a SMAD, a wingless (Wnt) complex protein, including beta-catenin, NOTCH, transforming growth factor beta (TGFβ), Activin, Nodal and glycogen synthase kinase 3β (GSK3 β) proteins, bone morphogenetic proteins (BMP), fibroblast growth factor receptor (FGFR), and Notch. For many cell surface receptors or internal receptor proteins, ligand-receptor interactions are not directly linked to the cell's response. The ligand activated receptor can first interact with other proteins inside the cell before the ultimate physiological effect of the ligand on the cell's behavior is produced. Often, the behavior of a chain of several interacting cell proteins is altered following receptor activation or inhibition. The entire set of cell changes induced by receptor activation is called a signal transduction mechanism or signaling pathway.

As used herein, the term "signals" refer to internal and external factors that control changes in cell structure and function. They can be chemical or physical in nature.

As used herein, the term "ligands" refers to molecules and proteins that bind to receptors, e.g., TGFβ, Activin, Nodal, BMPs, FGFRs, etc.

As used herein, the term "inhibitor", refers to a compound or molecule (e.g., small molecule, peptide, peptidomimetic, natural compound, siRNA, anti-sense nucleic acid, aptamer, or antibody) that interferes with (e.g., reduces, decreases, suppresses, eliminates, or blocks) the signaling function of the molecule or pathway. An inhibitor can be any compound or molecule that changes any activity of a named protein (signaling molecule, any molecule involved with the named signaling molecule, a named associated molecule, such as a GSK3β (e.g., including, but not limited to, the signaling molecules described herein), for one example, via directly contacting SMAD signaling, contacting SMAD mRNA, causing conformational changes of SMAD, decreasing SMAD protein levels, or interfering with SMAD interactions with signaling partners (e.g., including those described herein), and affecting the expression of SMAD target genes (e.g. those described herein). Inhibitors also include molecules that indirectly regulate SMAD biological activity by intercepting upstream signaling molecules (e.g., within the extracellular domain, examples of a signaling molecule and an effect include: Noggin which sequesters bone morphogenic proteins, inhibiting activation of ALK receptors 1, 2, 3, and 6, thus preventing downstream SMAD activation. Likewise, Chordin, Cerberus, Follistatin, similarly sequester extracellular activators of SMAD signaling. Bambi, a transmembrane protein, also acts as a pseudo-receptor to sequester extracellular TGFβ signaling molecules. Antibodies that block activins, nodal, TGFβ, and BMPs are contemplated for use to neutralize extracellular activators of SMAD signaling, and the like. Inhibitors are described in terms of competitive inhibition (binds to the active site in a manner as to exclude or reduce the binding of another known binding compound) and allostenc inhibition (binds to a protein in a manner to change the protein conformation in a manner which interferes with binding of a compound to that protein's active site) in addition to inhibition induced by binding to and affecting a molecule upstream from the named signaling molecule that in turn causes inhibition of the named molecule. An inhibitor can be a "direct inhibitor" that inhibits a signaling target or a signaling target pathway by actually contacting the signaling target.

As used herein, the term "activator" refers to compounds that increase, induce, stimulate, activate, facilitate, or enhance activation the signaling function of the molecule or pathway, e.g., Wnt signaling As used herein, the term "derivative" refers to a chemical compound with a similar core structure.

As used herein, the term "a population of cells" or "a cell population" refers to a group of at least two cells. In non-limiting examples, a cell population can include at least about 10, at least about 100, at least about 200, at least about 300, at least about 400, at least about 500, at least about 600, at least about 700, at least about 800, at least about 900, at least about 1000 cells. The population may be a pure population comprising one cell type, such as a population of proprioceptors, or a population of undifferentiated stem cells. Alternatively, the population may comprise more than one cell type, for example a mixed cell population.

As used herein, the term "stem cell" refers to a cell with the ability to divide for indefinite periods in culture and to give rise to specialized cells. A stem cell refers to a stem cell that is from a human.

As used herein, the term "embryonic stem cell" refers to a primitive (undifferentiated) cell that is derived from pre-implantation-stage embryo, capable of dividing without differentiating for a prolonged period in culture, and are known to develop into cells and tissues of the three primary germ layers. A human embryonic stem cell refers to an embryonic stem cell that is from a human. As used herein, the term "human embryonic stem cell" or "hESC" refers to a type of pluripotent stem cells derived from early stage human embryos, up to and including the blastocyst stage, that is capable of dividing without differentiating for a prolonged period in culture, and are known to develop into cells and tissues of the three primary germ layers.

As used herein, the term "embryonic stem cell line" refers to a population of embryonic stem cells which have been cultured under in vitro conditions that allow proliferation without differentiation for up to days, months to years.

As used herein, the term "totipotent" refers to an ability to give rise to all the cell types of the body plus all of the cell types that make up the extraembryonic tissues such as the placenta.

As used herein, the term "multipotent" refers to an ability to develop into more than one cell type of the body.

As used herein, the term "pluripotent" refers to an ability to develop into the three developmental germ layers of the organism including endoderm, mesoderm, and ectoderm.

As used herein, the term "induced pluripotent stem cell" or "iPSC" refers to a type of pluripotent stem cell, similar to an embryonic stem cell, formed by the introduction of certain embryonic genes (such as a OCT4, SOX2, and KLF4 transgenes) (see, for example, Takahashi and Yamanaka Cell 126, 663-676 (2006), herein incorporated by reference) into a somatic cell, for examples, CI 4, C72, and the like. An induced pluripotent stem cell may be prepared from any fully (e.g., mature or adult) or partially differentiated cell using methods known in the art. For example, but not by way of limitation, an induced pluripotent stem cell may be prepared from a fibroblast, such as a human fibroblast; an epithelial cell, such as a human epithelial cell; a blood cell such as a lymphocyte or hematopoietic cell or cell precursor or myeloid cell, such as a human lymphocyte, hematopoietic cell or cell precursor or human myeloid cell; or a renal epithelial cell, such as a human renal epithelial cell. In certain non-limiting embodiments, an induced pluripotent stem cell contains one or more introduced reprogramming factor associated with producing pluripotency. In certain non-limiting embodiments a human induced pluripotent stem cell is not identical to a human embryonic pluripotent stem cell.

As used herein, the term "somatic cell" refers to any cell in the body other than gametes (egg or sperm); sometimes referred to as "adult" cells.

As used herein, the term "somatic (adult) stem cell" refers to a relatively rare undifferentiated cell found in many organs and differentiated tissues with a limited capacity for both self-renewal (in the laboratory) and differentiation. Such cells vary in their differentiation capacity, but it is usually limited to cell types in the organ of origin.

As used herein, the term "neuron" refers to a nerve cell, the principal functional units of the nervous system. A neuron consists of a cell body and its processes—an axon and one or more dendrites. Neurons transmit information to other neurons or cells by releasing neurotransmitters at synapses.

As used herein, the term "proliferation" refers to an increase in cell number.

As used herein, the term "undifferentiated" refers to a cell that has not yet developed into a specialized cell type.

As used herein, the term "differentiation" refers to a process whereby an unspecialized embryonic cell acquires the features of a specialized cell such as a heart, liver, or muscle cell. Differentiation is controlled by the interaction of a cell's genes with the physical and chemical conditions outside the cell, usually through signaling pathways involving proteins embedded in the cell surface.

As used herein, the term "directed differentiation" refers to a manipulation of stem cell culture conditions to induce differentiation into a particular (for example, desired) cell type, such as proprioceptors (proprioceptive sensory neurons). As used herein, the term "directed differentiation" in reference to a stem cell refers to the use of small molecules, growth factor proteins, and other growth conditions to promote the transition of a stem cell from the pluripotent state into a more mature or specialized cell fate (e.g., proprioceptors).

As used herein, the term "inducing differentiation" in reference to a cell refers to changing the default cell type (genotype and/or phenotype) to a non-default cell type (genotype and/or phenotype). Thus, "inducing differentiation in a stem cell" refers to inducing the stem cell (e.g., stem cell) to divide into progeny cells with characteristics that are different from the stem cell, such as genotype (e.g., change in gene expression as determined by genetic analysis such as a microarray) and/or phenotype (e.g., change in expression of a protein, such as one or more proprioceptor marker, including, but not limited to, TrkC, Runx3, CDHL1, ETV1, and ETV4).

As used herein, the term "cell culture" refers to a growth of cells in vitro in an artificial medium for research or medical treatment.

As used herein, the term "culture medium" refers to a liquid that covers cells in a culture vessel, such as a Petri plate, a multi-well plate, and the like, and contains nutrients to nourish and support the cells. Culture medium may also include growth factors added to produce desired changes in the cells.

As used herein, the term "contacting" cells with a compound (e.g., one or more inhibitor, activator and/or BMP) refers to placing the compound in a location that will allow it to touch the cell. The contacting may be accomplished using any suitable methods. For example, contacting can be accomplished by adding the compound to a tube of cells. Contacting may also be accomplished by adding the compound to a culture medium comprising the cells. Each of the compounds (e.g., the inhibitors, activators and BMPs disclosed herein) can be added to a culture medium comprising the cells as a solution (e.g., a concentrated solution). Alternatively or additionally, the compounds (e.g., the inhibitors, activators, and BMPs disclosed herein) as well as the cells can be present in a formulated cell culture medium.

As used herein, the term "in vitro" refers to an artificial environment and to processes or reactions that occur within an artificial environment. In vitro environments exemplified, but are not limited to, test tubes and cell cultures.

As used herein, the term "in vivo" refers to the natural environment (e.g., an animal or a cell) and to processes or reactions that occur within a natural environment, such as embryonic development, cell differentiation, neural tube formation, etc.

As used herein, the term "expressing" in relation to a gene or protein refers to making an mRNA or protein which can be observed using assays such as microarray assays, antibody staining assays, and the like.

As used herein, the term "marker" or "cell marker" refers to gene or protein that identifies a particular cell or cell type. A marker for a cell may not be limited to one marker, markers may refer to a "pattern" of markers such that a designated group of markers may identity a cell or cell type from another cell or cell type.

As used herein, the term "derived from" or "established from" or "differentiated from" when made in reference to any cell disclosed herein refers to a cell that was obtained from (e.g., isolated, purified, etc.) a parent cell in a cell line, tissue (such as a dissociated embryo, or fluids using any manipulation, such as, without limitation, single cell isolation, cultured in vitro, treatment and/or mutagenesis using for example proteins, chemicals, radiation, infection with virus, transfection with DNA sequences, such as with a morphogen, etc., selection (such as by serial culture) of any cell that is contained in cultured parent cells. A derived cell can be selected from a mixed population by virtue of response to a growth factor, cytokine, selected progression of cytokine treatments, adhesiveness, lack of adhesiveness, sorting procedure, and the like.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "an effective amount" or "effective amounts" refers to an amount of a molecule (e.g., inhibitors of TGFβ/Activin-Nodal signaling, inhibitors of SMAD, activator of Wnt signaling, inhibitors of FGFR, inhibitors of Notch, and BMPs) that is sufficient to achieve the desired effects in directing the in vitro differentiating of stem cells into a population differentiated cells expressing one or more proprioceptor marker. In certain embodiments, the population of differentiated cells comprise cells expressing one or more nociceptor marker. In certain embodiments, the population of differentiated cells comprise cells expressing one or more mechanoreceptor marker.

5.2 Method of Differentiating Stem Cells

The presently disclosed subject matter provides for in vitro methods for inducing differentiation of stem cells (e.g., human stem cells). In certain embodiments, the stem cells are human stem cells. Non-limiting examples of human stem cells include human embryonic stem cells (hESC), human pluripotent stem cell (hPSC), human induced pluripotent stem cells (hiPSC), human parthenogenetic stem cells, primoridal germ cell-like pluripotent stem cells, epiblast stem cells, F-class pluripotent stem cells, somatic stem cells, cancer stem cells, or any other cell capable of lineage specific differentiation. In certain embodiments, the human stem cell is a human embryonic stem cell (hESC). In certain embodiments, the human stem cell is a human induced pluripotent stem cell (hiPSC). In certain embodiments, the stem cells are non-human stem cells. Non-limiting examples of non-human stem cells include non-human primate stem cells, rodent stem cells, dog stem cells, cat stem cells, horse stem cells, pig stem cells, etc. In certain embodiments, the stem cells are pluripotent stem cells. In certain embodiments, the stem cells are embryonic stem cells. In certain embodiments, the stem cells are induced pluripotent stem cells.

The inventors previously disclosed the use of dual SMAD inhibition for inducing differentiation of stem cells (e.g., hPSC) to one type of neural lineage (Chambers (2009), which is incorporated by reference in its entirety). Furthermore, the inventors previously disclosed differentiation of stem cells to nociceptors (neural crest derived cell lineage) by sequential inhibition of SMAD signaling followed by activation of Wnt signaling (Chambers (2012); International Patent Publication No. WO 2011/149762, which are incorporated by reference in their entireties). These neural crest (NC) differentiation methods and protocols result in $SOX10^+$ NC precursors that are HOX negative, which is indicative of anterior/cranial identify; cranial NC (CNCs), and these methods and protocols primarily give rise to sensory and nociceptive neurons.

The presently disclosed subject matter is based at least in part on the discovery that peripheral sensory neurons, e.g., proprioceptive sensory neurons (proprioceptors), can be differentiated from stem cells (e.g., human stem cells) by sequential inhibition of SMAD signaling followed by activation of Wnt signaling.

In certain embodiments, a presently disclosed differentiation method comprises contacting a population of stem cells (e.g., human stem cells) with an effective amount(s) of one or more inhibitor of TGFβ/Activin-Nodal signaling. In certain embodiments, the inhibitor of TGFβ/Activin-Nodal signaling neutralizes the ligands including TGFβs, bone morphogenetic proteins (BMPs), Nodal, and activins, or blocking their signal pathways through blocking the receptors and downstream effectors. Non-limiting examples of inhibitors of TGFβ/Activin-Nodal signaling are disclosed in WO2011/149762, Chambers (2009), and Chambers (2012), which are incorporated by reference in their entireties. In certain embodiments, the one or more inhibitor of TGFβ/

Activin-Nodal signaling is a small molecule selected from the group consisting of SB431542, derivatives thereof, and mixtures thereof.

In certain embodiments, the inhibitor of TGFβ/Activin-Nodal signaling is SB431542. "SB431542" refers to a molecule with a number CAS 301836-41-9, a molecular formula of $C_{22}K_8N_4O_3$, and a name of 4-[4-(1,3-benzodioxol-5-yl)-5-(2-pyridinyl)-1H-imidazol-2-yl]-benzamide, for example, see structure below:

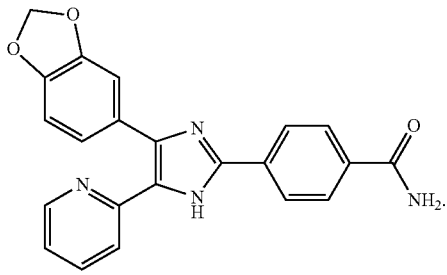 [SMILES: NC(=O)c1ccc(-c2nc(-c3ccc4c(c3)OCO4)c(-c3ccccn3)[nH]2)cc1]

In certain embodiments, the method comprises contacting the stem cells (e.g., human stem cells) with an effective amount(s) of one or more activator of Wnt signaling. As used herein, the term "WNT" or "wingless" in reference to a ligand refers to a group of secreted proteins (i.e. Int1 (integration 1) in humans) capable of interacting with a WNT receptor, such as a receptor in the Frizzled and LRPDerailed/RYK receptor family. As used herein, the term "WNT" or "wingless" in reference to a signaling pathway refers to a signal pathway composed of Wnt family ligands and Wnt family receptors, such as Frizzled and LRPDerailed/RYK receptors, mediated with or without β-catenin. For the purposes described herein, a preferred WNT signaling pathway includes mediation by β-catenin, e.g., WNT/-catenin.

In certain embodiments, the one or more activator of Wnt signaling lowers GSK3β for activation of Wnt signaling. Thus, the activator of Wnt signaling can be a GSK3β inhibitor. A GSK3β inhibitor is capable of activating a WNT signaling pathway, see e.g., Cadigan, et al., J Cell Sci. 2006; 119:395-402; Kikuchi, et al., Cell Signaling. 2007; 19:659-671, which are incorporated by reference herein in their entireties. As used herein, the term "glycogen synthase kinase 3β inhibitor" refers to a compound that inhibits a glycogen synthase kinase 3β enzyme, for example, see, Doble, et al., J Cell Sci. 2003; 116:1175-1186, which is incorporated by reference herein in its entirety.

Non-limiting examples of activators of Wnt signaling or GSK3β inhibitors are disclosed in WO2011/149762, Chambers (2012), and Calder et al., J Neurosci. 2015 Aug. 19; 35(33):11462-81, which are incorporated by reference in their entireties. In certain embodiments, the one or more activator of Wnt signaling is a small molecule selected from the group consisting of CHIR99021, derivatives thereof, and mixtures thereof "CHIR99021" (also known as "aminopyrimidine" or "3-[3-(2-Carboxyethyl)-4-methylpyrrol-2-methylidenyl]-2-indolinone") refers to IUPAC name 6-(2-(4-(2,4-dichlorophenyl)-5-(4-methyl-1H-imidazol-2-yl) pyrimidin-2-ylamino) ethylamino)nicotinonitrile with the following formula.

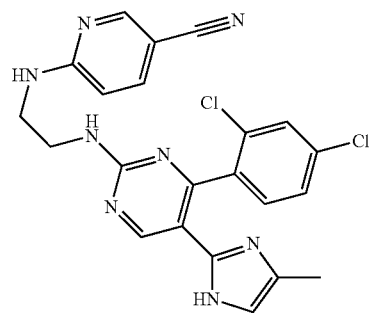 [SMILES: Cc1c[nH]c(-c2cnc(NCCNc3ccc(C#N)cn3)nc2-c2ccc(Cl)cc2Cl)n1]

In certain embodiments, the Wnt activator is CHIR99021. CHIR99021 is highly selective, showing nearly thousand-fold selectivity against a panel of related and unrelated kinases, with an IC50=6.7 nM against human GSK3β and nanomolar IC50 values against rodent GSK3β homologs.

In certain embodiments, the method further comprises contacting the stem cells (e.g., human stem cells) with an effective amount(s) of one or more inhibitor of SMAD signaling. Non-limiting examples of inhibitors of SMAD signaling are disclosed in WO2011/149762, Chambers (2009), and Chambers (2012), which are incorporated by reference in their entireties. In certain embodiments, the one or more inhibitor of SMAD signaling is a small molecule selected from the group consisting of LDN193189, derivatives thereof, and mixtures thereof.

In certain embodiments, the one or more inhibitor of SMAD signaling is LDN193189. "LDN193189" refers to a small molecule DM-3189, IUPAC name 4-(6-(4-(piperazin-1-yl)phenyl)pyrazolo[1,5-a]pyrimidin-3-yl)quinoline, with a chemical formula of $C_{25}H_{22}N_6$ with the following formula.

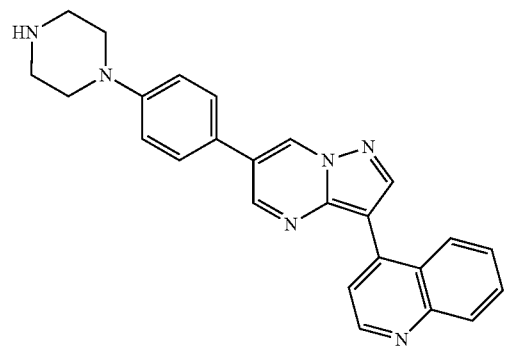 [SMILES: c1ccc2c(-c3cnn4cc(-c5ccc(N6CCNCC6)cc5)cnc34)ccnc2c1]

LDN193189 is capable of functioning as a SMAD signaling inhibitor. LDN193189 is also highly potent small-molecule inhibitor of ALK2, ALK3, and ALK6, protein tyrosine kinases (PTK), inhibiting signaling of members of the ALK1 and ALK3 families of type I TGFβ receptors, resulting in the inhibition of the transmission of multiple biological signals, including the bone morphogenetic proteins (BMP) BMP2, BMP4, BMP6, BMP7, and Activin cytokine signals and subsequently SMAD phosphorylation of Smad1, Smad5, and Smad8 (Yu et al. (2008) Nat Med 14:1363-1369; Cuny et al. (2008) Bioorg. Med. Chem. Lett. 18: 4388-4392, herein incorporated by reference).

In certain embodiments, the method further comprises contacting the stem cells (e.g., human stem cells) with an effective amount(s) of one or more inhibitor of FGFR family signaling. In certain embodiments, the FGFR family signaling comprises vascular endothelial growth factor (VEGF) receptors, fibroblast growth factor (FGF) receptors and platelet-derived growth factor (PDGF) tyrosine kinase receptors. Non-limiting examples of inhibitors of FGFR family signaling are disclosed in WO2011/149762 and Chambers (2009), which are incorporated by reference in their entireties. In certain embodiments, the one or more inhibitor of FGF receptor family signaling is a small molecule selected from the group consisting of SU5402, PD-161570, PD-173074, derivatives thereof, and mixtures thereof.

In certain embodiments, the one or more inhibitor of FGF receptor family signaling is SU5402. "SU5402" refers to a small molecule with a chemical formula of $C_{11}H_{16}N_2O_3$ and chemical name: 2-[(1,2-Dihydro-2-oxo-3H-indol-3-ylidene)methyl]-4-methyl-1H-pyrrole-3-propanoic acid (Sun et al (1999) Design, synthesis and evaluations of substituted 3-[(3- or 4-carboxyethylpyrrol-2-yl)methylidenyl]indolin-2-ones as inhibitors of VEGF, FGF and PDGF receptor tyrosine kinases. J. Med. Chem. 42 5120; Paterson et al (2004) Preclinical studies of fibroblast growth factor receptor 3 as a therapeutic target in multiple myeloma. Br. J. Haematol. 124 595; Tanaka et al (2005) FGF-induced vesicular release of sonic hedgehog and retmoic acid in leftward nodal flow is critical for left-right determination. Nature 435:172, herein incorporated by reference). SU5402 has the following formula.

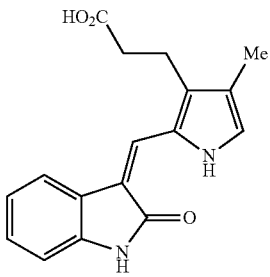 [SMILES: Cc1c[nH]c(/C=C2\C(=O)Nc3ccccc32)c1CCC(=O)O]

In certain embodiments, the one or more inhibitor of FGFR family signaling is PD 173074. "PD 173074" refers to a small molecule with a chemical name: N-[24 [4-(Diethylamino)butyl] amino]-6-(3,5-dimethoxyphenyl) pyrido [2,3-d]pyrimidin-7-yl]-N'-(1,1-dimethyl ethyl)urea (Bansal et al (2003) Specific inhibitor of FGF receptor signaling: FGF-2-mediated effects on proliferation, differentiation, and MAPK activation are inhibited by PD 173074 in oligodendrocyte-lineage cells. J. Neurosci. Res. 74:486, herein incorporated by reference).

In certain embodiments, the method further comprises contacting the stem cells (e.g., human stem cells) with an effective amount(s) of one or more inhibitor of Notch signaling. Non-limiting examples of inhibitors of Notch signaling are disclosed in WO2011/149762 and Chambers (2009), which are incorporated by reference in their entireties. The one or more inhibitor of Notch signaling can inhibit Notch activation. In certain embodiments, the one or more inhibitor of Notch signaling is one or more γ-secretase inhibitor. γ-secretase inhibitors are a class of agents which prevent the generation of the active domain of a Notch molecules resulting in suppressing downstream Notch signaling. Non-limiting examples of γ-secretase inhibitors are DAPT, a tripeptide aldehyde inhibitor, a γ-secretase inhibitor XII, LY-411,575. In certain embodiments, the one or more inhibitor of Notch signaling is a small molecule selected from the group consisting of are DAPT, a tripeptide aldehyde inhibitor, a γ-secretase inhibitor XII, LY-411,575, derivatives thereof, and mixtures thereof.

In certain embodiments, the one or more inhibitor of Notch signaling is DAPT. "DAPT" refers to a small molecule known as N-[(3,5-Difluorophenyl)acetyl]-L-alanyl-2-phenyl]glycine-1,1-dimethyl ethyl ester; LY-374973, N—[N-(3,5-Difluorophenacetyl)-L-alanyl]-S-phenylglycine t-butyl ester; or N—[N-(3,5-difluorophenacetyl)-L-alanyl]-S-phenylglycine t-butyl ester. DAPT has a chemical formula of $C_{23}H_{26}F_2N_2O_4$ with the following formula.

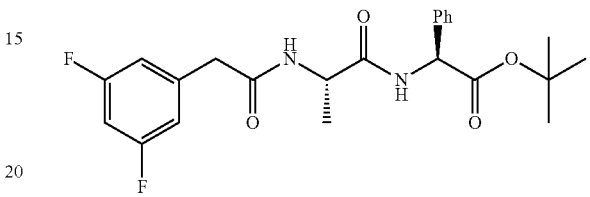

In certain embodiments, the one or more inhibitor of Notch signaling is a DAPT derivative, e.g., DAP-BpB (a photoactivable DAPT derivative) with a chemical name of (N—[N-(3,5-difluorophenacetyl)-L-alanyl]-(S)-phenylglycine-4-(4-(8-biotinamido)octylamino)benzoyl)benzyl)methylamide).

In certain embodiments, the method comprises contacting the stem cells with an effective amount(s) of one or more BMP. Non-limiting examples of BMP include BMP2, BMP4, BMP6, and BMP7. In certain embodiments, the one or more BMP is BMP4.

In certain embodiments, the above-described inhibitors, activator(s) and BMP(s) are added to a cell culture medium comprising the stem cells. Suitable cell culture media include, but are not limited to, Knockout® Serum Replacement ("KSR") medium, N2 medium, and an Essential 8®/Essential 6® ("E8/E6") medium. KSR medium, N2 medium, E8/E6 medium are commercially available. The cell culture medium used for culturing the presently disclosed population of stem cells not only determines the inhibitor(s) to be contacted with the stem cells (e.g., for a KSR medium, one or more inhibitor of TGFβ/Activin-Nodal signaling and one or more inhibitor of SMAD signaling are required; and for an E8/E6 medium, only one or more inhibitor of TGFβ/Activin-Nodal signaling is required, and optionally one or more BMP is added), but also determines the sequence of contacting the above-described inhibitor(s) and activator(s) with the stem cells.

In certain embodiments, the cell culture medium is a KSR medium. A KSR medium is a defined, serum-free formulation optimized to grow and maintain undifferentiated hESC cells in culture. The components of a KSR medium are disclosed in WO2011/149762. In certain embodiments, a KSR medium comprises Knockout DMEM, Knockout Serum Replacement, L-Glutamine, Pen/Strep, MEM, and 13-mercaptoethanol. In certain embodiments, 1 liter of KSR medium comprises 820 mL of Knockout DMEM, 150 mL of Knockout Serum Replacement, 10 mL of 200 mM L-Glutamine, 10 mL of Pen/Strep, 10 mL of 10 mM MEM, and 55 μM of 13-mercaptoethanol.

In certain embodiments, the stem cells are contacted with one or more inhibitor of TGFβ/Activin-Nodal signaling, one or more inhibitor of SMAD signaling, and one or more activator of Wnt signaling. In certain embodiments, one or more inhibitor of TGFβ/Activin-Nodal signaling, one or more inhibitor of SMAD signaling, and one or more activator of Wnt signaling are added to a cell culture medium comprising the stem cells. In certain embodiments, the stem cells are further contacted with one or more inhibitor of FGFR family signaling and one or more inhibitor of Notch signaling. In certain embodiments, one or more inhibitor of TGFβ/Activin-Nodal signaling, one or more inhibitor of SMAD signaling, one or more activator of Wnt signaling, one or more inhibitor of FGFR family signaling, and one or more inhibitor of Notch signaling are added to a cell culture medium comprising the stem cells. In certain embodiments, the initial contact of the stem cells with the one or more inhibitor of TGFβ/Activin-Nodal signaling is on the same day (within the same 24 hour period) as the initial contact of the stem cells with the one or more inhibitor of SMAD signaling, e.g., by initially adding these inhibitors to a cell culture medium comprising the stem cells (e.g., a KSR medium) on the same day. In certain embodiments, the initial contact of the cells with the one or more activator of Wnt signaling is between about 1 day and about 4 day (e.g., about 1 day, about 2 days, about 3 days, or about 4 days) from the initial contact of the stem cells with the one or more inhibitor of TGFβ/Activin-Nodal signaling. In certain embodiments, the initial contact of the cells with the one or more activator of Wnt signaling is about 2 days after the initial contact of the stem cells with the one or more inhibitor of TGFβ/Activin-Nodal signaling. In certain embodiments, the initial contact of the cells with the one or more activator of Wnt signaling is on the same day (within the same 24 hour period) as the initial contact of the cells with the one or more inhibitor of FGFR family signaling and one or more inhibitor of Notch signaling.

In certain embodiments, the stem cells are contacted with the one or more inhibitor of TGFβ/Activin-Nodal signaling and the one or more inhibitor of SMAD signaling for at least about 10 days, e.g., for between about 10 days and about 30 days, for between about 10 days and about 20 days, for between about 10 days and about 15 days. In certain embodiments, the cells are contacted with the one or more inhibitor of TGFβ/Activin-Nodal signaling and the one or more inhibitor of SMAD signaling for at least about 11 days. In certain embodiments, the cells are contacted with the one or more inhibitor of TGFβ/Activin-Nodal signaling and the one or more inhibitor of SMAD signaling for at least about 12 days. In certain embodiments, the one or more inhibitor of TGFβ/Activin-Nodal signaling and the one or more inhibitor of SMAD signaling are added daily to a cell culture medium comprising the stem cells from day 0 through day 11. In certain embodiments, the one or more inhibitor of TGFβ/Activin-Nodal signaling and the one or more inhibitor of SMAD signaling are added every other day to a cell culture medium comprising the stem cells (e.g., a KSR medium) from day 0 through day 11 (e.g., added on day 0, day 2, day 4, day 6, day 8, and day 10).

In certain embodiments, the stem cells are contacted with the one or more activator of Wnt signaling for at least about 5 days, e.g., for between about 5 days and about 30 days, for between about 5 days and about 15 days, for between about 5 days and about 10 days, or for between about 10 days and about 15 days. In certain embodiments, the stem cells are contacted with the one or more activator of Wnt signaling for about 10 days. In certain embodiments, the stem cells are contacted with the one or more activator of Wnt signaling for about 9 days. In certain embodiments, the one or more activator of Wnt signaling is added daily to a cell culture medium comprising the stem cells (e.g., a KSR medium) from day 2 through day 11. In certain embodiments, the one or more activator of Wnt signaling is added every other day to a cell culture medium comprising the stem cells (e.g., a KSR medium) from day 2 through day 11 (e.g., added on day 2, day 4, day 6, day 8, and day 10).

In certain embodiments, the stem cells are further contacted with one or more inhibitor of FGFR family signaling. In certain embodiments, the stem cells are further contacted with one or more inhibitor of Notch signaling. In certain embodiments, the initial contact of the cells with the one or more activator of Wnt signaling is on the same day (within the same 24 hour period) as the initial contact of the cells with the one or more inhibitor of FGFR family signaling and the one or more inhibitor of Notch signaling (e.g., by initially adding these inhibitors and the Wnt signaling activator(s) to a cell culture medium comprising the stem cells (e.g., a KSR medium) on the same day). In certain embodiments, the stem cells are contacted with the one or more inhibitor of FGFR family signaling and the one or more inhibitor of Notch signaling for at least about 5 days, e.g., for between about 5 days and about 30 days, for between about 5 days and about 15 days, for between about 5 days and about 10 days, or for between about 10 days and about 15 days. In certain embodiments, the stem cells are contacted with the one or more inhibitor of FGFR family signaling, and the one or more inhibitor of Notch signaling for about 10 days. In certain embodiments, the stem cells are contacted with the one or more inhibitor of FGFR family signaling, and the one or more inhibitor of Notch signaling for about 9 days. In certain embodiments, the stem cells are contacted with the one or more inhibitor of FGFR family signaling, and the one or more inhibitor of Notch signaling for about 11 days. In certain embodiments, the one or more inhibitor of FGFR family signaling, and the one or more inhibitor of Notch signaling are added daily to a cell culture medium comprising the stem cells (e.g., a KSR medium) from day 2 through day 11. In certain embodiments, the one or more inhibitor of FGFR family signaling, and the one or more inhibitor of Notch signaling are added every other day to a cell culture medium comprising the stem cells (e.g., a KSR medium) from day 2 through day 11 (e.g., added on day 2, day 4, day 6, day 8, and day 10).

In certain embodiments, the cells are contacted with the one or more inhibitor of TGFβ/Activin-Nodal signaling and the one or more inhibitor of SMAD signaling from day 0 through day 11, and the cells are contacted with the one or more activator of Wnt signaling, the one or more inhibitor of FGFR family signaling, and the one or more inhibitor of Notch signaling from day 2 through day 11.

In certain embodiments, the one or more inhibitor of TGFβ/Activin-Nodal signaling and the one or more inhibitor of SMAD signaling are added daily to a cell culture medium comprising the stem cells (e.g., a KSR medium) from day 0 through day 11, and the one or more activator of Wnt signaling, the one or more inhibitor of FGFR family signaling, and the one or more inhibitor of Notch signaling are added daily to a cell culture medium comprising the stem cells (e.g., a KSR medium) from day 2 through day 11. In certain embodiments, the one or more inhibitor of TGFβ/Activin-Nodal signaling and the one or more inhibitor of SMAD signaling are added every other day to a cell culture medium comprising the stem cells (e.g., a KSR medium) from day 0 through day 11 (e.g., added on day 0, day 2, day 4, day 6, day 8, and day 10), and the one or more activator of Wnt signaling, the one or more inhibitor of FGFR family signaling, and the one or more inhibitor of Notch signaling are added every other day to a cell culture medium comprising the stem cells (e.g., a KSR medium) from day 2 through day 11 (e.g., added on day 2, day 4, day 6, day 8, and day 10).

In certain embodiments, the cell culture medium is an E8/E6 medium. An E8/E6 medium is more defined than a KSR medium. E8/E6 medium is a feeder-free and xeno-free medium that supports the growth and expansion of human pluripotent stem cells. E8/E6 medium has been proven to support somatic cell reprogramming. In addition, E8/E6 medium can be used as a base for the formulation of custom media for the culture of PSCs. One example E8/E6 medium is described in Chen et al., *Nat Methods* 2011 May; 8(5): 424-9, which is incorporated by reference in its entirety. One example E8/E6 medium is disclosed in WO2015/077648, which is incorporated by reference in its entirety. One example E8/E6 medium for differentiating stem cells to neural crest cells is disclosed in PCT/US17/16723, which is incorporated by reference in its entirety.

In certain embodiments, an E8/E6 cell culture medium comprises DMEM/F12, ascorbic acid, selenium, insulin, NaHCO$_3$, transferrin, FGF2 and TGFβ. The E8/E6 medium differs from a KSR medium in that E8/E6 medium does not include an active BMP or Wnt ingredient. Thus, in certain embodiments, when an E8/E6 medium is used to culture the presently disclosed population of stem cells to differentiate into a population of proprioceptors, one or more inhibitor of SMAD signaling (e.g., those inhibiting BMP) is not required to be added to the E8/E6 medium. In certain embodiments, the stem cells are contacted with one or more inhibitor of TGFβ/Activin-Nodal signaling and one or more activator of Wnt signaling. In certain embodiments, one or more inhibitor of TGFβ/Activin-Nodal signaling and one or more activator of Wnt signaling are added to a cell culture medium comprising the stem cells. In certain embodiments, the initial contact of the stem cells with the one or more activator of Wnt signaling is on the same day (within the same 24 hour period) as the initial contact of the one or more inhibitor of TGFβ/Activin-Nodal signaling. In certain embodiments, the stem cells are contacted with one or more bone morphogenetic protein (BMP) active agent. BMPs are a group of growth factors providing pivotal morphogenetic signals, orchestrating tissue architecture throughout the body. In certain embodiments, one or more BMP is added to a cell culture medium comprising the stem cells. In certain embodiments, the initial contact of the stem cells with the one or more BMP is on the same day (within the same 24 hour period) as the initial contact of the one or more inhibitor of TGFβ/Activin-Nodal signaling and one or more activator of Wnt signaling, e.g., by adding the inhibitor(s), activator(s) and BMP(s) to a cell culture medium comprising the stem cells (e.g., an E8/E6 medium) on the same day. In certain embodiments, the stem cells are contacted with the one or more BMP for up to about 2 days. In certain embodiments, the stem cells are contacted with the one or more BMP for about 2 days.

In certain embodiments, the stem cells are contacted with the one or more inhibitor of TGFβ/Activin-Nodal signaling and the one or more activator of Wnt signaling for at least about 10 days, e.g., for between about 10 days and about 30 days, for between about 10 days and about 20 days, for between about 10 days and about 15 days. In certain embodiments, the stem cells are contacted with the one or more inhibitor of TGFβ/Activin-Nodal signaling and the one or more activator of Wnt signaling for at least about 12 days. In certain embodiments, the stem cells are contacted with the one or more inhibitor of TGFβ/Activin-Nodal signaling and the one or more activator of Wnt signaling for at least about 13 days. In certain embodiments, the one or more inhibitor of TGFβ/Activin-Nodal signaling and the one or more activator of Wnt signaling are added daily to a cell culture medium comprising the stem cells (e.g., an E8/E6 medium) from day 0 through day 11. In certain embodiments, the one or more inhibitor of TGFβ/Activin-Nodal signaling and the one or more activator of Wnt signaling are added daily to a cell culture medium comprising the stem cells (e.g., an E8/E6 medium) from day 0 through day 12. In certain embodiments, the one or more inhibitor of TGFβ/Activin-Nodal signaling and the one or more activator of Wnt signaling are added daily to a cell culture medium comprising the stem cells (e.g., an E8/E6 medium) from day 0 through day 12. In certain embodiments, the one or more inhibitor of TGFβ/Activin-Nodal signaling and the one or more activator of Wnt signaling are added every other day to a cell culture medium comprising the stem cells (e.g., an E8/E6 medium) from day 0 through day 12 (e.g., added on day 0, day 2, day 4, day 6, day 8, day 10, and day 12). In certain embodiments, the one or more BMP is added daily to a cell culture medium comprising the stem cells (e.g., an E8/E6 medium) from day 0 through day 1.

In certain embodiments, the stem cells are further contacted with one or more inhibitor of FGFR family signaling. In certain embodiments, the stem cells are further contacted with one or more inhibitor of Notch signaling. In certain embodiments, the initial contact of the cells with the one or more inhibitor of FGFR family signaling and the one or more inhibitor of Notch signaling is about 2 days from the initial contact of the cells with the one or more activator of Wnt signaling. In certain embodiments, one or more inhibitor of TGFβ/Activin-Nodal signaling, one or more BMP, one or more activator of Wnt signaling, one or more inhibitor of FGFR family signaling, and one or more inhibitor of Notch signaling are added to a cell culture medium comprising the stem cells (e.g., an E8/E6 medium).

In certain embodiments, the stem cells are further contacted with one or more inhibitor of FGFR family signaling. In certain embodiments, the stem cells are further contacted with one or more inhibitor of Notch signaling. In certain embodiments, the initial contact of the cells with the one or more inhibitor of FGFR family signaling and the one or more inhibitor of Notch signaling is within an about 4 day period (e.g., on the same day, or 1 day, or 2 days, or 3 days, or 4 days later) from the initial contact of the cells with the one or more activator of Wnt signaling. In certain embodiments, the initial contact of the cells with the one or more inhibitor of FGFR family signaling and the one or more inhibitor of Notch signaling is about 2 days from the initial contact of the cells with the one or more activator of Wnt signaling. In certain embodiments, the stem cells are contacted with the one or more inhibitor of FGFR family signaling and the one or more inhibitor of Notch signaling for at least about 5 days, e.g., for between about 5 days and about 30 days, for between about 5 days and about 15 days, for between about 5 days and about 10 days, or for between about 10 days and about 15 days. In certain embodiments, the stem cells are contacted with the one or more inhibitor of FGFR family signaling and the one or more inhibitor of Notch signaling for about 10 days. In certain embodiments, the stem cells are contacted with the one or more inhibitor of FGFR family signaling and the one or more inhibitor of Notch signaling for about 9 days. In certain embodiments, the stem cells are contacted with the one or more inhibitor of FGFR family signaling and the one or more inhibitor of Notch signaling for about 11 days. In certain embodiments, the one or more inhibitor of FGFR family signaling, and the one or more inhibitor of Notch signaling are added daily to a cell culture medium comprising the stem cells (e.g., an E8/E6 medium) from day 2 through day 12. In certain embodiments, the one or more inhibitor of FGFR family signaling and the one or more inhibitor of Notch signaling are added daily to a cell culture medium comprising the stem cells (e.g., an E8/E6 medium) from day 2 through day 12. In certain embodiments, the one or more inhibitor of FGFR family signaling, and the one or more inhibitor of Notch signaling are added every other day to a cell culture medium comprising the stem cells (e.g., an E8/E6 medium) from day 2 through day 12 (e.g., added on day 2, day 4, day 6, day 8, day 10 and day 12).

In certain embodiments, the one or more inhibitor of TGFβ/Activin-Nodal signaling and the one or more activator of Wnt signaling are added daily to a cell culture medium comprising the stem cells (e.g., an E8/E6 medium) from day 0 through day 12, and the one or more BMP is added daily to a cell culture medium comprising the stem cells (e.g., an E8/E6 medium) from day 0 through day 1, and the one or more inhibitor of FGFR family signaling and the one or more inhibitor of Notch signaling are added daily to a cell culture medium comprising the stem cells (e.g., an E8/E6 medium) from day 2 through day 12. In certain embodiments, the one or more inhibitor of TGFβ/Activin-Nodal signaling and the one or more activator of Wnt signaling are added every other day to a cell culture medium comprising the stem cells (e.g., an E8/E6 medium) from day 0 through day 12 (e.g., added on day 0, day 2, day 4, day 6, day 8, day 10, and day 12), and the one or more BMP is added daily to a cell culture medium comprising the stem cells (e.g., an E8/E6 medium) from day 0 through day 1, and the one or more inhibitor of FGFR family signaling and the one or more inhibitor of Notch signaling are added every other day to a cell culture medium comprising the stem cells (e.g., an E8/E6 medium) from day 2 through day 12 (e.g., added on day 2, day 4, day 6, day 8, day 10 and day 12).

In certain embodiments, the methods disclosed herein can be used for differentiating stem cells into peripheral sensory neurons, including nociceptors, proprioceptors and mechanoceptors. In certain embodiments, the methods disclosed herein differentiate a population of stem cells into a population of cells expressing one or more marker selected from the group consisting of proprioceptor markers, nociceptor markers, mechanoceptor markers, and peripheral sensory neuron markers. Non-limiting examples of proprioceptor markers include TrkC, RUNX3, CDHL1, ETV1, and ETV4. Non-limiting examples of nociceptor markers include TrkA and RUNX1. Non-limiting examples of mechanoreceptor markers include TrkB and RET. Non-limiting examples of peripheral sensory neuron markers include Brn3A, peripherin, and ISL1.

N2 supplement is a chemically defined, animal-free, supplement used for expansion of undifferentiated neural stem and progenitor cells in culture. N2 Supplement is intended for use with DMEM/F12 medium. The components of a N2 medium are disclosed in WO2011/149762. In certain embodiments, a N2 medium comprises a DMEM/F12 medium supplemented with glucose, sodium bicarbonate, putrescine, progesterone, sodium selenite, transferrin, and insulin. In certain embodiments, 1 liter of a N2 medium comprises 985 ml dist. H$_2$O with DMEM/F12 powder, 1.55 g of glucose, 2.00 g of sodium bicarbonate, putrescine (100 μL aliquot of 1.61 g dissolved in 100 mL of distilled water), progesterone (20 μL aliquot of 0.032 g dissolved in 100 mL 100% ethanol), sodium selenite (60 μL aliquot of 0.5 mM solution in distilled water), 100 mg of transferrin, and 25 mg of insulin in 10 mL of 5 mM NaOH. In certain embodiments, the stem cells are initially cultured in a KSR medium, which is gradually replaced with increasing amount of a N2 medium from about 1, about 2, about 3, about 4, about 5, about 6, about 7 about 8 days after the initial contact of the stem cells with at least one of the above-described inhibitors and activators. In certain embodiments, the stem cells are initially cultured in a KSR medium, which is gradually replaced with increasing amount of a N2 medium starting from about day 4 from initial contact of the stem cells with at least one of the above-described inhibitors and activators.

The stem cells can be contacted with the one or more inhibitor of TGFβ/Activin-Nodal signaling for at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days. In certain embodiments, the stem cells are contacted with the one or more inhibitor of TGFβ/Activin-Nodal signaling for up to about 8 days, up to about 9 days, up to about 10 days, up to about 11 days, up to about 12 days up to about 13 days, up to about 14 days, up to about 15 days, up to about 16 days, up to about 17 days, up to about 18 days, up to about 19 days, or up to about 20 days. In certain embodiments, the stem cells are contacted with the one or more inhibitor of TGFβ/Activin-Nodal signaling for between about 8 days and about 20 days, between about 8 days and about 10 days, between about 10 days and about 12 days, between about 8 days and about 15 days, between about 12 days and about 15 days, between about 15 days and about 20 days, between about 10 days and about 15 days, or between about 10 days and about 20 days. In certain embodiments, the stem cells are contacted with the one or more inhibitor of TGFβ/Activin-Nodal signaling for between 10 days and about 15 days. In certain embodiments, the stem cells are contacted with the one or more inhibitor of TGFβ/Activin-Nodal signaling for about 8 days, about 9 days, about 10 days, about 11 days, about 12 days, about 13 days, about 14 days, about 15 days, about 16 days, about 17 days, about 18 days, about 19 days, or about 20 days. In certain embodiments, the stem cells are contacted with the one or more inhibitor of TGFβ/Activin-Nodal signaling for about 13 days. In certain embodiments, the stem cells are contacted with the one or more inhibitor of TGFβ/Activin-Nodal signaling for about 12 days. In certain embodiments, the stem cells are contacted with the one or more inhibitor of TGFβ/Activin-Nodal signaling for about 11 days.

The stem cells can be contacted with the one or more activator of Wnt signaling for at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days. In certain embodiments, the stem cells are contacted with the one or more activator of Wnt signaling for up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, or up to about 20 days. In certain embodiments, the stem cells are contacted with the one or more activator of Wnt signaling for between about 5 days and about 15 days, between about 5 days and about 10 days, between about 10 days and about 15 days, between about 15 days and about 20 days, or between about 10 days and about 20 days. In certain embodiments, the stem cells are contacted with the one or more activator of Wnt signaling for between 5 days and about 15 days. In certain embodiments, the stem cells are contacted with the one or more activator of Wnt signaling for about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, or about 20 days. In certain embodiments, the stem cells are contacted with the one or more activator of Wnt signaling for about 10 days. In certain embodiments, the stem cells are contacted with the one or more activator of Wnt signaling for about 9 days. In certain embodiments, the stem cells are contacted with the one or more activator of Wnt signaling for about 12 days. In certain embodiments, the stem cells are contacted with the one or more activator of Wnt signaling for about 11 days. In certain embodiments, the stem cells are contacted with the one or more activator of Wnt signaling for about 13 days. In certain embodiments, the stem cells are contacted with the one or more activator of Wnt signaling for about 12 days.

The stem cells can be contacted with the one or more inhibitor of SMAD signaling for at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days. In certain embodiments, the stem cells are contacted with the one or more inhibitor of SMAD signaling for up to about 8 days, up to about 9 days, up to about 10 days, up to about 11 days, up to about 12 days up to about 13 days, up to about 14 days, up to about 15 days, up to about 16 days, up to about 17 days, up to about 18 days, up to about 19 days, or up to about 20 days. In certain embodiments, the stem cells are contacted with the one or more inhibitor of SMAD signaling for between about 8 days and about 20 days, between about 8 days and about 10 days, between about 10 days and about 12 days, between about 12 days and about 15 days, between about 15 days and about 20 days, between about 10 days and about 15 days, or between about 10 days and about 20 days. In certain embodiments, the stem cells are contacted with the one or more inhibitor of SMAD signaling for between 10 days and about 15 days. In certain embodiments, the stem cells are contacted with the one or more inhibitor of SMAD signaling for about 8 days, about 9 days, about 10 days, about 11 days, about 12 days, about 13 days, about 14 days, about 15 days, about 16 days, about 17 days, about 18 days, about 19 days, or about 20 days. In certain embodiments, the stem cells are contacted with the one or more inhibitor of SMAD signaling for about 12 days. In certain embodiments, the stem cells are contacted with the one or more inhibitor of SMAD signaling for about 11 days.

The stem cells can be contacted with the one or more inhibitor of FGFR family signaling for at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days. In certain embodiments, the stem cells are contacted with the one or more inhibitor of FGFR family signaling for up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, or up to about 20 days. In certain embodiments, the stem cells are contacted with the one or more inhibitor of FGFR family signaling for between about 5 days and about 15 days, between about 5 days and about 10 days, between about 10 days and about 15 days, between about 15 days and about 20 days, or between about 10 days and about 20 days. In certain embodiments, the stem cells are contacted with the one or more inhibitor of FGFR family signaling for between 5 days and about 15 days. In certain embodiments, the stem cells are contacted with the one or more inhibitor of FGFR family signaling for about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, or about 20 days. In certain embodiments, the stem cells are contacted with the one or more inhibitor of FGFR family signaling for about 10 days. In certain embodiments, the stem cells are contacted with the one or more inhibitor of FGFR family signaling for about 9 days. In certain embodiments, the stem cells are contacted with the one or more inhibitor of FGFR family signaling for about 12 days. In certain embodiments, the stem cells are contacted with the one or more inhibitor of FGFR family signaling for about 11 days.

The stem cells can be contacted with the one or more inhibitor of Notch signaling for at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days. In certain embodiments, the stem cells are contacted with the one or more inhibitor of Notch signaling for up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, or up to about 20 days. In certain embodiments, the stem cells are contacted with the one or more inhibitor of Notch signaling for between about 5 days and about 15 days, between about 5 days and about 10 days, between about 10 days and about 15 days, between about 15 days and about 20 days, or between about 10 days and about 20 days.

In certain embodiments, the stem cells are contacted with the one or more inhibitor of Notch signaling for between 5 days and about 15 days. In certain embodiments, the stem cells are contacted with the one or more inhibitor of Notch signaling for about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, or about 20 days. In certain embodiments, the stem cells are contacted with the one or more inhibitor of Notch signaling for about 10 days. In certain embodiments, the stem cells are contacted with the one or more inhibitor of Notch signaling for about 9 days. In certain embodiments, the stem cells are contacted with the one or more inhibitor of Notch signaling for about 12 days. In certain embodiments, the stem cells are contacted with the one or more inhibitor of Notch signaling for about 11 days.

In certain embodiments, the stem cells are contacted with one or more inhibitor of TGFβ/Activin-Nodal signaling and the one or more inhibitor of SMAD signaling for about 12 days; and with the one or more activator of Wnt signaling for about 10 days. In certain embodiments, the stem cells are further contacted with the one or more inhibitor of FGFR family signaling and the one or more inhibitor of Notch signaling for about 10 days. In certain embodiments, the stem cells are contacted with one or more inhibitor of TGFβ/Activin-Nodal signaling and the one or more inhibitor of SMAD signaling for about 11 days, and with the one or more activator of Wnt signaling for about 9 days. In certain embodiments, the stem cells are further contacted with the one or more inhibitor of FGFR family signaling, and the one or more inhibitor of Notch signaling for about 9 days. In certain embodiments, the cell culture medium to which the one or more inhibitor of TGFβ/Activin-Nodal signaling, the one or more inhibitor of SMAD signaling, the one or more activator of Wnt signaling, the one or more inhibitor of FGFR family signaling, and the one or more inhibitor of Notch signaling are added is a KSR medium.

In certain embodiments, the stem cells are contacted with one or more inhibitor of TGFβ/Activin-Nodal signaling and the one or more activator of Wnt signaling for about 13 days, and with the one or more BMP for about 2 days. In certain embodiments, the stem cells are further contacted with the one or more inhibitor of FGFR family signaling, and the one or more inhibitor of Notch signaling for about 11 days. In certain embodiments, the cell culture medium to which the one or more inhibitor of TGFβ/Activin-Nodal signaling, the one or more activator of Wnt signaling, the one or more BMP, one or more inhibitor of FGFR family signaling, and the one or more inhibitor of Notch signaling are added is an E8/E6 medium.

In certain embodiments, the stem cells are contacted with the one or more inhibitor of TGFβ/Activin-Nodal signaling in a concentration of from about 1 nM to about 300 nM, from about 5 nM to about 250 nM, from about 10 nM to about 200 nM, from about 10 nM to about 50 nM, from about 5 nM to about 20 nM, from about 5 nM to about 15 nM, from about 5 nM to about 30 nM, from about 5 nM to about 40 nM, from about 50 nM to about 150 nM, from about 80 nM to about 120 nM, from about 90 nM to about 110 nM, from about 50 nM to about 100 nM, from about 100 nM to about 150 nM, from about 150 nM to about 200 nM, from about 200 nM to about 250 nM, or from about 250 nM to about 300 nM. In certain embodiments, the stem cells are contacted with the one or more inhibitor of TGFβ/Activin-Nodal signaling in a concentration of from about 80 nM to about 120 nM. In certain embodiments, the stem cells are contacted with the one or more inhibitor of TGFβ/Activin-Nodal signaling in a concentration of about 100 nM. In certain embodiments, the stem cells are contacted with the one or more inhibitor of TGFβ/Activin-Nodal signaling in a concentration of about 10 nM. In certain embodiments, the stem cells are contacted with the one or more inhibitor of TGFβ/Activin-Nodal signaling in any one of the above-described concentrations daily. In certain embodiments, the stem cells are contacted with the one or more inhibitor of TGFβ/Activin-Nodal signaling in a concentration of about 100 nM daily. In certain embodiments, the stem cells are contacted with the one or more inhibitor of TGFβ/Activin-Nodal signaling in a concentration of about 10 nM daily.

In certain embodiments, the stem cells are contacted with the one or more inhibitor of SMAD signaling in a concentration of from about 1 μM to about 100 from about 1 μM to about 20 from about 1 μM to about 15 from about 1 μM to about 10 from about 1 μM to about 5 from about 5 μM to about 10 from about 5 μM to about 15 from about 15 μM to about 20 from about 20 μM to about 30 from about 30 μM to about 40 from about 40 μM to about 50 from about 50 μM to about 60 from about 60 μM to about 70 from about 70 μM to about 80 from about 80 μM to about or from about 90 μM to about 100 μM. In certain embodiments, the stem cells are contacted with the one or more inhibitor of SMAD signaling in a concentration of from about from about 5 μM to about 15 μM. In certain embodiments, the stem cells are contacted with the one or more inhibitor of SMAD signaling in a concentration of about 10 μM. In certain embodiments, the stem cells are contacted with the one or more inhibitor of SMAD signaling in any one of the above-described concentrations daily. In certain embodiments, the stem cells are contacted with the one or more inhibitor of SMAD signaling in a concentration of about 10 μM daily.

In certain embodiments, the stem cells are contacted with the one or more activator of Wnt signaling in a concentration of from about from about 0.1 μM to about 10 μM, e.g., from about 0.1 μM to about 5 or from about 5 μM to about 10 μM. In certain embodiments, the stem cells are contacted with the one or more activator of Wnt signaling in a concentration of less than about 3 μM, e.g., from about 0.1 μM to about 0.5 from about 0.1 μM to about from about 0.1 μM to about 1.5 from about 0.1 μM to about 2 from about 0.1 μM to about 2.5 from about 0.5 μM to about 1 from about 0.5 μM to about 1.5 from about 0.5 μM to about 2 from about 0.5 μM to about 2.5 from about 1 μM to about 1.5 from about 1 μM to about 2 from about 1 μM to about 2.5 from about 1.5 μM to about 2 from about 1.5 μM to about 2.5 or from about 2 μM to about 2.5 μM. In certain embodiments, the stem cells are contacted with the one or more activator of Wnt signaling in a concentration of less than about 1.5 μM or less than 1.0 μM, e.g., from about 0.05 μM to about 1.5 from about 0.1 μM to about 1.0 from about 0.1 μM to about 0.5 or from about 0.5 μM to about 1.0 μM. In certain embodiments, the stem cells are contacted with the one or more activator of Wnt signaling in a concentration of from about 0.1 μM to 2.5 μM. In certain embodiments, the stem cells are contacted with the one or more activator of Wnt signaling in a concentration of about 1.5 μM. In certain embodiments, the stem cells are contacted with the one or more activator of Wnt signaling in a concentration of from about 0.1 μM to 1.0 μM. In certain embodiments, the stem cells are contacted with the one or more activator of Wnt signaling in a concentration of about 0.6 μM. In certain embodiments, the stem cells are contacted with the one or more activator of Wnt signaling in any one of the above-described concentrations daily. In certain embodiments, the stem cells are contacted with the one or more activator of Wnt signaling in a concentration of about 1.5 μM daily.

In certain embodiments, the cell culture medium to which the one or more activator of Wnt signaling is added is an E8/E6 medium, and the concentration of the one or more activator of Wnt signaling added to the E8/E6 medium on the first two days are different (e.g., lower) from the concentration of the one or more activator of Wnt signaling added after two days, e.g., on day 2 and after (e.g., from day 2 through day 12). In certain embodiments, the stem cells are contacted daily with the one or more activator of Wnt signaling on day 0 and day 1 at a concentration of less than about 1.0 μM (e.g., from about 0.1 μM to about 1.0 μM, e.g., about 0.6 In certain embodiments, the stem cells are contacted daily with the one or more activator of Wnt signaling from day 2 through day 12 at a concentration of less than about 3.0 μM (e.g., from about 0.1 μM to about 2.5 μM, e.g., about 1.5 μM. In certain embodiments, the stem cells are contacted with the one or more activator of Wnt signaling in any one of the above-described concentrations daily.

In certain embodiments, the stem cells are contacted with one or more BMP in a concentration of up to about 2 ng/ml, e.g., from about 0.05 to about 2 ng/mL, from about 0.05 ng/mL to about 0.1 ng/ml, from about 0.1 ng/mL to about 2 ng/ml, from about 0.1 ng/mL to about 1.5 ng/ml, from about 0.5 ng/mL to about 1.5 ng/ml, or from about 1.5 to about 2 ng/ml. In certain embodiments, the stem cells are contacted with one or more BMP in a concentration of from about 0.5 ng/mL to about 1.5 ng/ml. In certain embodiments, the stem cells are contacted with one or more BMP in a concentration of about 1 ng/ml. In certain embodiments the stem cells are contacted with one or more BMP in a concentration of about 0.25 ng/ml. In certain embodiments, the stem cells are contacted with one or more BMP in a concentration of about 0.5 ng/ml. In certain embodiments, the stem cells are contacted with the one or more BMP in any one of the above-described concentrations daily.

In certain embodiments, the stem cells are contacted with the one or more inhibitor of FGFR family signaling in a concentration of from about 1 µM to about 100 from about 1 µM to about 20 from about 1 µM to about 15 from about 1 µM to about 10 from about 1 µM to about 5 from about 5 µM to about 10 from about 5 µM to about 15 from about 15 µM to about 20 from about 20 µM to about 30 from about 30 µM to about 40 from about 40 µM to about 50 from about 50 µM to about 60 µM, from about 60 µM to about 70 from about 70 µM to about 80 from about 80 µM to about 90 µM, or from about 90 µM to about 100 µM. In certain embodiments, the stem cells are contacted with the one or more inhibitor of FGFR family signaling in a concentration of from about 5 µM to about 15 µM. In certain embodiments, the stem cells are contacted with the one or more inhibitor of FGFR family signaling in a concentration of about 10 µM. In certain embodiments, the stem cells are contacted with the one or more inhibitor of FGFR family signaling in a concentration of up to 10 µM or up to 7.5 µM (e.g., about 1 about 2 about 3 about 4 about 5 about 6 about 7 or about 7.5 µM. In certain embodiments, the stem cells are contacted with the one or more inhibitor of FGFR family signaling in a concentration of about 5 µM. In certain embodiments, the stem cells are contacted with the one or more inhibitor of FGFR family signaling in any one of the above-described concentrations daily. In certain embodiments, the stem cells are contacted with the one or more inhibitor of FGFR family signaling in a concentration of about 10 µM daily. In certain embodiments, the stem cells are contacted with the one or more inhibitor of FGFR family signaling in a concentration of about 5 µM daily.

In certain embodiments, the stem cells are contacted with the one or more inhibitor of Notch signaling in a concentration of from about 1 µM to about 100 from about 1 µM to about 20 from about 1 µM to about 15 from about 1 µM to about 10 from about 1 µM to about 5 from about 5 µM to about 10 from about 5 µM to about 15 from about 15 µM to about 20 from about 20 µM to about 30 from about 30 µM to about 40 from about 40 µM to about 50 from about 50 µM to about 60 µM, from about 60 µM to about 70 from about 70 µM to about 80 from about 80 µM to about 90 µM, or from about 90 µM to about 100 µM. In certain embodiments, the stem cells are contacted with the one or more inhibitor of Notch signaling in a concentration of from about 5 µM to about 15 µM. In certain embodiments, the stem cells are contacted with the one or more inhibitor of Notch signaling in a concentration of about 10 µM. In certain embodiments, the stem cells are contacted with the one or more inhibitor of Notch signaling in a concentration of up to 10 µM or up to 7.5 µM (e.g., about 1 about 2 about 3 about 4 about 5 about 6 about 7 or about 7.5 µM. In certain embodiments, the stem cells are contacted with the one or more inhibitor of Notch signaling in a concentration of about 5 µM. In certain embodiments, the stem cells are contacted with the one or more inhibitor of Notch signaling in any one of the above-described concentrations daily. In certain embodiments, the stem cells are contacted with the one or more inhibitor of Notch signaling in a concentration of about 10 µM daily. In certain embodiments, the stem cells are contacted with the one or more inhibitor of Notch signaling in a concentration of about 5 µM daily.

Proprioceptors (proprioceptive sensory neurons) (e.g., cells that express one or more proprioceptor marker) can be differentiated from stem cells (e.g., human stem cells) in less than about 20 days, less than about 19 days, less than about 18 days, less than about 17 days, less than about 16 days, less than about 15 days, less than about 14 days, less than about 13 days, less than about 12 days, less than about 11 days, less than about 10 days, less than about 9 days, less than about 8 days, less than about 7 days, less than about 6 days, less than about 5 days, or less than about 4 days after initial contact with the one or more inhibitor of TGFβ/Activin-Nodal signaling. In certain embodiments, proprioceptors are differentiated from stem cells on or after about 12 days after initial contact with the one or more inhibitor of TGFβ/Activin-Nodal signaling. In certain embodiments, proprioceptors are differentiated from stem cells on about 12 days after the initial contact with the one or more inhibitor of TGFβ/Activin-Nodal signaling. In certain embodiments, proprioceptors are differentiated from stem cells on or after about 11 days after the initial contact with the one or more inhibitor of TGFβ/Activin-Nodal signaling. In certain embodiments, proprioceptors are differentiated from stem cells on about 11 days after initial contact with the one or more inhibitor of TGFβ/Activin-Nodal signaling. In certain embodiments, proprioceptors are differentiated from stem cells on or after about 13 days after the initial contact with the one or more inhibitor of TGFβ/Activin-Nodal signaling. In certain embodiments, proprioceptors are differentiated from stem cells on about 13 days after the initial contact with the one or more inhibitor of TGFβ/Activin-Nodal signaling.

The differentiated cells express one or more proprioceptor marker. In certain embodiments, the proprioceptor marker is selected from the group consisting of TrkC, Runx3, CDHL1, ETV1, and ETV4.

The differentiated cells can further express one or more reporter. Non-limiting examples of reporters include fluorescent proteins (such as green fluorescent protein (GFP), blue fluorescent protein (EBFP, EBFP2, Azurite, mKalamal), cyan fluorescent protein (ECFP, Cerulean, CyPet, mTurquoise2), and yellow fluorescent protein derivatives (YFP, Citrine, Venus, YPet, EYFP)), β-galactosidase (LacZ), chloramphenicol acetyltransferase (cat), neomycin phosphotransferase (neo), enzymes (such as oxidases and peroxidases); and antigenic molecules. As used herein, the terms "reporter gene" or "reporter construct" refer to genetic constructs comprising a nucleic acid encoding a protein that is easily detectable or easily assayable, such as a colored protein, fluorescent protein such as GFP or an enzyme such as beta-galactosidase (lacZ gene).

The differentiated cells can be purified after differentiation, e.g., in a cell culture medium As used herein, the terms "purified," "purify," "purification," "isolated," "isolate," and "isolation" refer to the reduction in the amount of at least one contaminant from a sample. For example, a desired cell type is purified by at least 10%, by at least 30%, by at least 50%, by at least 75%, and by at least 90%>, with a corresponding reduction in the amount of undesirable cell types. The term "purify" can refer to the removal of certain cells (e.g., undesirable cells) from a sample. The removal or selection of non-proprioceptor results in an increase in the percent of desired proprioceptors in the sample. In certain embodiments, the cells are purified by sorting a mixed cell population into cells expressing at least one proprioceptor marker, e.g., TrkC, Brn3A, peripherin, ISL1, RUNX3, CDHL1, ETV1, and ETV4.

The presently disclosed subject matter also provides a population of in vitro differentiated cells expressing one or more proprioceptor marker produced by the methods described herein, and compositions comprising such in vitro differentiated cells.

5.3 Compositions Comprising Differentiated Cell Populations

The presently disclosed subject matter provides compositions comprising a population of differentiated proprioceptor cells produced by the in vitro differentiation methods described herein. In certain non-limiting embodiments, the differentiated proprioceptor cells are prepared from embryonic pluripotent stem cells, such as human embryonic pluripotent stem cells. In certain non-limiting embodiments, the differentiated proprioceptor cells are prepared from induced pluripotent stem cells, such as induced human pluripotent stem cells.

Furthermore, the presently disclosed subject matter provides compositions comprising a population of in vitro differentiated cells, wherein at least about 70% (e.g., at least about 75%, at least about 80%, at least about 85%, at least about 90%, at least about 95%, at least about 99%, or at least about 99.5%) of the population of cells express one or more proprioceptor marker, and wherein less than about 15% (e.g., less than about 10%, less than about 5%, less than about 4%, less than about 3%, less than about 2%, less than about 1%, less than about 0.5%, or less than about 0.1%) of the population of cells express one or more marker selected from the group consisting of peripheral sensory neuron markers, nociceptor markers, mechanoreceptor markers, stem cell markers, CNS markers, Cranial Neural Crest (CNC) markers, Melanocyte-competent Neural Crest (MNC) markers, neuronal cell markers, and mesenchymal precursor markers.

Furthermore, the presently disclosed subject matter provides compositions comprising a population of in vitro differentiated cells, wherein at least about 10% (e.g., at least about 20%, e.g., about 30%) of the population of cells express one or more proprioceptor marker, at least about 10% (e.g., at least about 20%, e.g., about 30%) of the population of cells express one or more nociceptor marker, at least about 10% (e.g., at least about 20%, e.g., about 30%) of the population of cells express one or more mechanoreceptor marker, and wherein less than about 15% (e.g., less than about 10%, less than about 5%, less than about 4%, less than about 3%, less than about 2%, less than about 1%, less than about 0.5%, or less than about 0.1%) of the population of cells express one or more marker selected from the group consisting of peripheral sensory neuron markers, stem cell markers, central nervous system (CNS) markers, Cranial Neural Crest (CNC) markers, Melanocyte-competent Neural Crest (MNC) markers, neuronal cell markers, and mesenchymal precursor markers.

Non-limiting examples of proprioceptor markers include TrkC, RUNX3, CDHL1, ETV1, and ETV4.

Non-limiting examples of peripheral sensory neuron markers include Brn3A, peripherin, and ISL1.

Non-limiting examples of nociceptor markers include TrkA and RUNX1.

Non-limiting examples of mechanoreceptor markers include TrkB and RET.

Non-limiting examples of stem cell markers include OCT4, NANOG, SOX2, LIN28, SSEA4 and SSEA3.

Non-limiting examples of CNS markers include PAX6, NESTIN, Vimentin, FOXG1, SOX2, TBR1, TBR2 and SOX1.

Non-limiting examples of neuronal cell markers include TUJ1, MAP2, NFH, BRN3A, ISL1, TH, ASCL1, CHAT, PHOX2B, PHOX2A, TRKA, TRKB, TRKC, 5HT, GABA, NOS, SST, TH, CHAT, DBH, Substance P, VIP, NPY, GnRH, and CGRP.

Non-limiting examples of mesenchymal precursor markers are SMA, Vimentin, HLA-ABC, CD105, CD90 and CD73.

Non-limiting examples of CNC markers include PAX6, NESTIN, Vimentin, FOXG1, SOX2, TBR1, TBR2 and SOX1.

Non-limiting examples of MNC markers include PAX6, NESTIN, Vimentin, FOXG1, SOX2, TBR1, TBR2 and SOX1.

In certain embodiments, the composition comprises a population of from about $1\times10^4$ to about $1\times10^{10}$ from about $1\times10^4$ to about $1\times10^5$ from about $1\times10^5$ to about $1\times10^9$ from about $1\times10^5$ to about $1\times10^6$, from about $1\times10^5$ to about $1\times10^7$, from about $1\times10^6$ to about $1\times10^7$, from about $1\times10^6$ to about $1\times10^8$, from about $1\times10^7$ to about $1\times10^8$, from about $1\times10^8$ to about $1\times10^9$, from about $1\times10^8$ to about $1\times10^{10}$, or from about $1\times10^9$ to about $1\times10^{10}$ of cells expressing one or more proprioceptor marker. In certain embodiments, the composition comprises a population of from about $1\times10^5$ to about $1\times10^7$ of cells expressing one or more proprioceptor marker.

In certain non-limiting embodiments, the composition further comprises a biocompatible scaffold or matrix, for example, a biocompatible three-dimensional scaffold that facilitates tissue regeneration when the cells are implanted or grafted to a subject. In certain non-limiting embodiments, the biocompatible scaffold comprises extracellular matrix material, synthetic polymers, cytokines, collagen, polypeptides or proteins, polysaccharides including fibronectin, laminin, keratin, fibrin, fibrinogen, hyaluronic acid, heparin sulfate, chondroitin sulfate, agarose or gelatin, and/or hydrogel. (See, e.g., U.S. Publication Nos. 2015/0159135, 2011/0296542, 2009/0123433, and 2008/0268019, the contents of each of which are incorporated by reference in their entireties).

In certain embodiments, the composition is a pharmaceutical composition that comprises a pharmaceutically acceptable carrier, excipient, diluent or a combination thereof. In certain embodiments, the compositions can be used to treat or prevent a disorder of proprioceptor neurons. In certain embodiments, the compositions can be used for preventing and/or treating a disorder of proprioceptor neurons and/or a neurodegenerative disease or disorder, e.g., Friedreich's Ataxia or Parkinson's disease.

5.4 Method of Preventing and/or Treating Disorders

In certain embodiments the in vitro differentiated cells that express one or more proprioceptor marker (also referred to as "stem-cell-derived proprioceptor") and a composition comprising thereof (e.g., a composition disclosed herein) can be used for preventing and/or treating a disorder of proprioceptor neurons. In certain embodiments the in vitro differentiated cells that express one or more proprioceptor marker (also referred to as "stem-cell-derived proprioceptor") and a composition comprising thereof (e.g., a composition disclosed herein) can be used for preventing and/or treating a disorder of proprioceptor neurons and/or a neurodegenerative disorder. The presently disclosed subject matter provides for methods of preventing and/or treating a disorder of proprioceptor neurons and/or a neurodegenerative disorder comprising administering to a subject suffering from said disorder a therapeutically effective amount of the presently disclosed stem-cell-derived proprioceptor or a composition comprising thereof (e.g., a composition disclosed herein). Furthermore, the presently disclosed subject matter provides for uses of the presently disclosed stem-cell-derived proprioceptor or a composition comprising thereof (e.g., a composition disclosed herein) for preventing and/or treating a disorder of proprioceptor neurons and/or a neurodegenerative disorder. Non-limiting examples of neurodegenerative disorders include Friedreich's ataxia, and Parkinson's disease. In certain embodiments, the neurodegenerative disorder is Friedreich's ataxia.

The presently disclosed stem-cell-derived proprioceptors or compositions comprising thereof (e.g., the compositions disclosed herein) can be administered or provided systemically or directly to a subject for preventing and/or treating a disorder of proprioceptor neurons and/or a neurodegenerative disorder. In certain embodiments, the presently disclosed stem-cell-derived proprioceptors or compositions comprising thereof (e.g., the compositions disclosed herein) are directly injected into an organ of interest (e.g., an organ affected by a disorder of proprioceptor neurons and/or a neurodegenerative disorder).

The presently disclosed stem-cell-derived proprioceptors or compositions comprising thereof (e.g., the compositions disclosed herein) can be administered in any physiologically acceptable vehicle. Pharmaceutical compositions comprising the presently disclosed stem-cell-derived proprioceptors and a pharmaceutically acceptable carrier are also provided. The presently disclosed stem-cell-derived proprioceptors and the pharmaceutical compositions comprising thereof can be administered via localized orthotropic (OT) injection, local application, systemic injection, intravenous injection, or parenteral administration.

The presently disclosed stem-cell-derived proprioceptors and the pharmaceutical compositions comprising thereof can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof. Sterile injectable solutions can be prepared by incorporating the compositions of the presently disclosed subject matter, e.g., a composition comprising the presently disclosed stem-cell-derived proprioceptors, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the presently disclosed subject matter, however, any vehicle, diluent, or additive used would have to be compatible with the presently disclosed stem-cell-derived proprioceptors.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the presently disclosed stem-cell-derived proprioceptors. This will present no problem to those skilled in chemical and pharmaceutical principles, or problems can be readily avoided by reference to standard texts or by simple experiments (not involving undue experimentation), from this disclosure and the documents cited herein.

An "therapeutically effective amount" is an amount sufficient to affect a beneficial or desired clinical result upon treatment. A therapeutically effective amount can be administered to a subject in one or more doses. In terms of treatment, a therapeutically effective amount is an amount that is sufficient to palliate, ameliorate, stabilize, reverse or slow the progression of the disorder of proprioceptive neurons and/or neurodegenerative disorder, or otherwise reduce the pathological consequences of the disorder of proprioceptive neurons and/or neurodegenerative disorder. The therapeutically effective amount is generally determined by the physician on a case-by-case basis and is within the skill of one in the art. Several factors are typically taken into account when determining an appropriate dosage to achieve a therapeutically effective amount. These factors include age, sex and weight of the subject, the condition being treated, the severity of the condition and the form and effective concentration of the cells administered.

The quantity of cells to be administered will vary for the subject being treated. In certain embodiments, from about $1 \times 10^4$ to about $1 \times 10^{10}$, from about $1 \times 10^4$ to about $1 \times 10^5$, from about $1\times10^5$ to about $1\times10^9$, from about $1\times10^5$ to about $1\times10^6$, from about $1\times10^5$ to about $1\times10^7$, from about $1\times10^6$ to about $1\times10^7$, from about $1\times10^6$ to about $1\times10^8$, from about $1\times10^7$ to about $1\times10^8$, from about $1\times10^8$ to about $1\times10^9$, from about $1\times10^8$ to about $1\times10^{10}$, or from about $1\times10^9$ to about $1\times10^{10}$ the presently disclosed stem-cell-derived proprioceptor are administered to a subject. The precise determination of what would be considered a therapeutically effective dose may be based on factors individual to each subject, including their size, age, sex, weight, and condition of the particular subject. Dosages can be readily ascertained by those skilled in the art from this disclosure and the knowledge in the art.

5.5. Kits

The presently disclosed subject matter provides for kits for inducing differentiation of stem cells. In certain embodiments, the kit comprises one or more inhibitor of TGFβ/Activin-Nodal signaling and one or more activator of Wnt signaling, and instructions for inducing differentiation of the stem cells into a population of differentiated cells that express one or more proprioceptor marker.

In certain embodiments, the instructions comprise contacting the stem cells with the inhibitor(s) and activator(s) in a specific sequence. The sequence of contacting the inhibitor(s) and activator(s) can be determined by the cell culture medium used for culturing the stem cells.

In certain embodiments, the instructions comprise initially contacting the stem cells with an effective amount(s) of the one or more activator of Wnt signaling within an about 4 day period (e.g., on the same day, about 1 day, about 2 days, about 3 days, or about 4 days later) beginning with the initial contact of the stem cells with the one or more inhibitor of TGFβ/Activin-Nodal signaling. In certain embodiments, the instructions comprise initially contacting the stem cells with the one or more inhibitor of TGFβ/Activin-Nodal signaling on the same day (within the same 24 hour period) as the initial contact of the cells with the one or more activator of Wnt signaling. In certain embodiments, the instructions comprise initially contacting the stem cells with the one or more activator of Wnt signaling between about 1 day and about 4 days following the initial contact with the one or more inhibitor of TGFβ/Activin-Nodal signaling. In certain embodiments, the instructions comprise initially contacting the cells with the one or more activator of Wnt signaling about 2 days following the initial contact with of the stem cells with the one or more inhibitor of TGFβ/Activin-Nodal signaling.

In certain embodiments, the kit further comprises one or more inhibitor of SMAD signaling. In certain embodiments, the instructions comprise initially contacting the stem cells with the one or more inhibitor of TGFβ/Activin-Nodal signaling on the same day (within the same 24 hour period) as the initial contact of the stem cells with the one or more inhibitor of SMAD signaling.

In certain embodiments, the kit further comprises one or more BMP. In certain embodiments, the instructions comprise initially contacting the stem cells with the one or more inhibitor of TGFβ/Activin-Nodal signaling on the same day (within the same 24 hour period) as the initial contact of the stem cells with the one or more BMP. In certain embodiments, the instructions comprise contacting the stem cells with the one or more BMP for up to about 2 days.

In certain embodiments, the kit further comprises one or more inhibitor of FGF family signaling. In certain embodiments, the kit further comprises one or more inhibitor of Notch signaling. In certain embodiments, the instructions comprise initially contacting the cells with the one or more inhibitor of Notch signaling on the same day (within the same 24 hour period) as the initial contact of the one or more inhibitor of FGF family signaling. In certain embodiments, the instructions comprise initially contacting the cells with the one or more inhibitor of Notch signaling and the one or more inhibitor of FGF family signaling about 2 days from the initial contact of the cells with the one or more activator of the Wnt signaling. In certain embodiments, the instructions comprise initially contacting the cells with the one or more inhibitor of Notch signaling and the one or more inhibitor of FGF family signaling on the same day (within the same 24 hour period) from the initial contact of the cells with the one or more activator of the Wnt signaling.

In certain embodiments, the instructions comprise contacting the stem cells with the one or more inhibitor of TGFβ/Activin-Nodal signaling for at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days. In certain embodiments, the instructions comprise contacting the stem cells with the one or more inhibitor of TGFβ/Activin-Nodal signaling for up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, or up to about 20 days. In certain embodiments, the instructions comprise contacting the stem cells with the one or more inhibitor of TGFβ/Activin-Nodal signaling for between about 8 days and about 20 days, between about 8 days and about 10 days, between about 10 days and about 12 days, between about 12 days and about 15 days, between about 15 days and about 20 days, between about 10 days and about 15 days, or between about 10 days and about 20 days. In certain embodiments, the instructions comprise contacting the stem cells with the one or more inhibitor of TGFβ/Activin-Nodal signaling for between 10 days and about 15 days. In certain embodiments, the instructions comprise contacting the stem cells with the one or more inhibitor of TGFβ/Activin-Nodal signaling for about 8 days, about 9 days, about 10 days, about 11 days, about 12 days, about 13 days, about 14 days, about 15 days, about 16 days, about 17 days, about 18 days, about 19 days, or about 20 days. In certain embodiments, the instructions comprise contacting the stem cells with the one or more inhibitor of TGFβ/Activin-Nodal signaling for about 12 days. In certain embodiments, the instructions comprise contacting the stem cells with the one or more inhibitor of TGFβ/Activin-Nodal signaling for about 11 days. In certain embodiments, the instructions comprise contacting the stem cells with the one or more inhibitor of TGFβ/Activin-Nodal signaling for about 13 days.

In certain embodiments, the instructions comprise contacting the stem cells with the one or more inhibitor of SMAD signaling for at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days. In certain embodiments, the instructions comprise contacting the stem cells with the one or more inhibitor of SMAD signaling for up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, or up to about 20 days. In certain embodiments, the instructions comprise contacting the stem cells with the one or more inhibitor of SMAD signaling for between about 8 days and about 20 days, between about 8 days and about 10 days, between about 10 days and about 12 days, between about 12 days and about 15 days, between about 15 days and about 20 days, between about 10 days and about 15 days, or between about 10 days and about 20 days. In certain embodiments, the instructions comprise contacting the stem cells with the one or more inhibitor of SMAD signaling for between 10 days and about 15 days. In certain embodiments, the instructions comprise contacting the stem cells with the one or more inhibitor of SMAD signaling for about 8 days, about 9 days, about 10 days, about 11 days, about 12 days, about 13 days, about 14 days, about 15 days, about 16 days, about 17 days, about 18 days, about 19 days, or about 20 days. In certain embodiments, the instructions comprise contacting the stem cells with the one or more inhibitor of SMAD signaling for about 12 days. In certain embodiments, the instructions comprise contacting the stem cells with the one or more inhibitor of SMAD signaling for about 11 days.

In certain embodiments, the instructions comprise contacting the stem cells with the one or more activator of Wnt signaling for at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days. In certain embodiments, the instructions comprise contacting the stem cells with the one or more activator of Wnt signaling for up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, or up to about 20 days. In certain embodiments, the instructions comprise contacting the stem cells with the one or more activator of Wnt signaling for between about 5 days and about 15 days, between about 5 days and about 10 days, between about 10 days and about 15 days, between about 15 days and about 20 days, or between about 10 days and about 20 days. In certain embodiments, the instructions comprise contacting the stem cells with the one or more activator of Wnt signaling for between 5 days and about 15 days. In certain embodiments, the instructions comprise contacting the stem cells with the one or more activator of Wnt signaling for about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, or about 20 days. In certain embodiments, the instructions comprise contacting the stem cells with the one or more activator of Wnt signaling for about 12 days. In certain embodiments, the instructions comprise contacting the stem cells with the one or more activator of Wnt signaling for about 11 days. In certain embodiments, the instructions comprise contacting the stem cells with the one or more activator of Wnt signaling for about 10 days. In certain embodiments, the instructions comprise contacting the stem cells with the one or more activator of Wnt signaling for about 9 days. In certain embodiments, the instructions comprise contacting the stem cells with the one or more activator of Wnt signaling for about 13 days.

In certain embodiments, the instructions comprise contacting the stem cells with the one or more inhibitor of FGFR family signaling for at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days. In certain embodiments, the instructions comprise contacting the stem cells with the one or more inhibitor of FGFR family signaling for up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, or up to about 20 days. In certain embodiments, the instructions comprise contacting the stem cells with the one or more inhibitor of FGFR family signaling for between about 5 days and about 15 days, between about 5 days and about 10 days, between about 10 days and about 15 days, between about 15 days and about 20 days, or between about 10 days and about 20 days. In certain embodiments, the instructions comprise contacting the stem cells with the one or more inhibitor of FGFR family signaling for between 5 days and about 15 days. In certain embodiments, the instructions comprise contacting the stem cells with the one or more inhibitor of FGFR family signaling for about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, or about 20 days. In certain embodiments, the instructions comprise contacting the stem cells with the one or more inhibitor of FGFR family signaling for about 11 days. In certain embodiments, the instructions comprise contacting the stem cells with the one or more inhibitor of FGFR family signaling for about 12 days. In certain embodiments, the instructions comprise contacting the stem cells with the one or more inhibitor of FGFR family signaling for about 10 days. In certain embodiments, the instructions comprise contacting the stem cells with the one or more inhibitor of FGFR family signaling for about 9 days.

In certain embodiments, the instructions comprise contacting the stem cells with the one or more inhibitor of Notch signaling for at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days. In certain embodiments, the instructions comprise contacting the stem cells with the one or more inhibitor of Notch signaling for up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, or up to about 20 days. In certain embodiments, the instructions comprise contacting the stem cells with the one or more inhibitor of Notch signaling for between about 5 days and about 15 days, between about 5 days and about 10 days, between about 10 days and about 15 days, between about 15 days and about 20 days, or between about 10 days and about 20 days. In certain embodiments, the instructions comprise contacting the stem cells with the one or more inhibitor of Notch signaling for between 5 days and about 15 days. In certain embodiments, the instructions comprise contacting the stem cells with the one or more inhibitor of Notch signaling for about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, or about 20 days. In certain embodiments, the instructions comprise contacting the stem cells with the one or more inhibitor of Notch signaling for about 12 days. In certain embodiments, the instructions comprise contacting the stem cells with the one or more inhibitor of Notch signaling for about 11 days. In certain embodiments, the instructions comprise contacting the stem cells with the one or more inhibitor of Notch signaling for about 10 days. In certain embodiments, the instructions comprise contacting the stem cells with the one or more inhibitor of Notch signaling for about 9 days.

In certain embodiments, the instructions comprise contacting the stem cells with one or more inhibitor of TGFβ/Activin-Nodal signaling and the one or more inhibitor of SMAD signaling for about 12 days; and contacting the stem cells with the one or more activator of Wnt signaling for about 10 days. In certain embodiments, the instructions further comprise contacting the stem cells with the one or more inhibitor of FGFR family signaling and the one or more inhibitor of Notch signaling for about 10 days. In certain embodiments, the instructions comprise contacting the stem cells with one or more inhibitor of TGFβ/Activin-Nodal signaling and the one or more inhibitor of SMAD signaling for about 11 days; contacting the stem cells with the one or more activator of Wnt signaling for about 9 days. In certain embodiments, the instructions further comprise contacting the stem cells with the one or more inhibitor of FGFR family signaling and the one or more inhibitor of Notch signaling for about 9 days. In certain embodiments, the instructions comprise contacting the stem cells with one or more inhibitor of TGFβ/Activin-Nodal signaling and the one or more activator of Wnt signaling for about 13 days; and contacting the stem cells with the one or more BMP for about 2 days. In certain embodiments, the instructions further comprise contacting the stem cells with the one or more inhibitor of FGFR family signaling and the one or more inhibitor of Notch signaling for about 11 days.

Furthermore, the presently disclosed subject matter provides for kits for treating and/or preventing a disorder of proprioceptor neurons and/or a neurodegenerative disorder. In certain embodiments, the kit comprises an effective amount of a population of the presently disclosed stem-cell-derived proprioceptors or a composition comprising such proprioceptors in unit dosage form. In certain embodiments, the kit comprises a sterile container which contains the therapeutic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain embodiments, the kit comprises instructions for administering a population of the presently disclosed stem-cell-derived proprioceptors or a composition comprising thereof to a subject suffering from a disorder of proprioceptor neurons and/or a neurodegenerative disorder. The instructions can comprise information about the use of the cells or composition for treating and/or preventing a disorder of proprioceptor neurons and/or a neurodegenerative disorder. In certain embodiments, the instructions comprise at least one of the following: description of the therapeutic agent; dosage schedule and administration for treating and/or preventing a disorder of proprioceptor neurons and/or a neurodegenerative disorder or symptoms thereof; precautions; warnings; indications; counter-indications; over dosage information; adverse reactions; animal pharmacology; clinical studies; and/or references. The instructions can be printed directly on the container (when present), or as a label applied to the container, or as a separate sheet, pamphlet, card, or folder supplied in or with the container.

EXAMPLES

The presently disclosed subject matter will be better understood by reference to the following Example, which is provided as exemplary of the presently disclosed subject matter, and not by way of limitation.

Example 1—Cell Culturing Methods for Inducing Proprioceptors from Human Stem Cells Human embryonic stem cells (hESCs) were cultured on mouse embryonic fibroblasts (MEFs, Globalstem, Rockville, State of Maryland, United States of America (USA)) in a medium comprising Dulbecco's Modified Eagle Medium (DMEM)/F12, 20% knockout serum replacement, 2 mM L-glutamine (Invitrogen, Carlsbad, State of California, USA), 100 µM MEM non-essential amino acids (Invitrogen). 10 ng/ml Fibroblast growth factor 2 (FGF-2, R&D Systems, Minneapolis, State of Minnesota) was added after sterile filtration and cells were fed daily and passaged weekly.

Figure 1B:
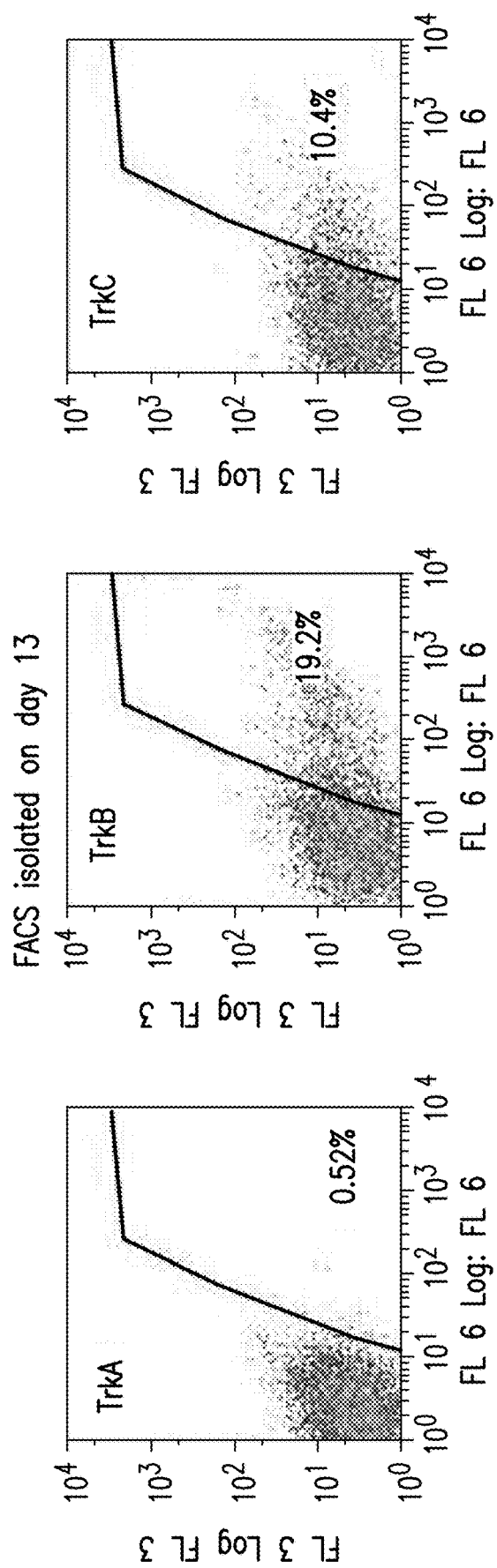
Figure 1C:
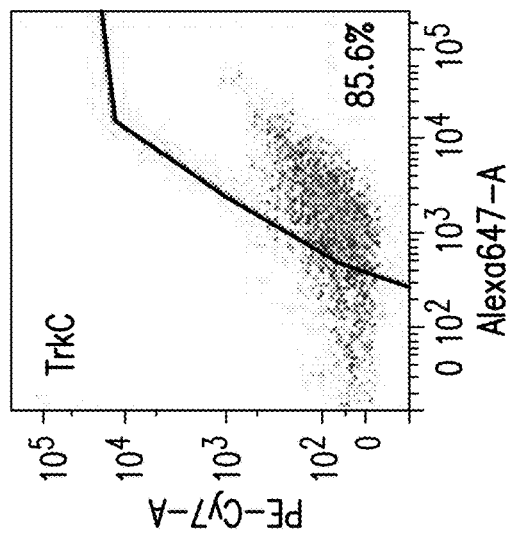
Figure 1C:
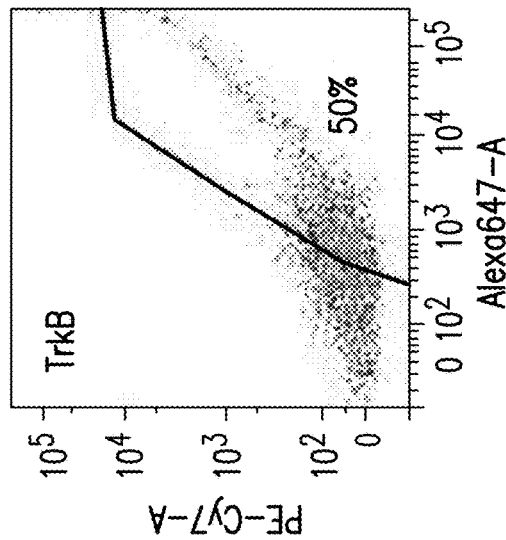
Figure 1D:
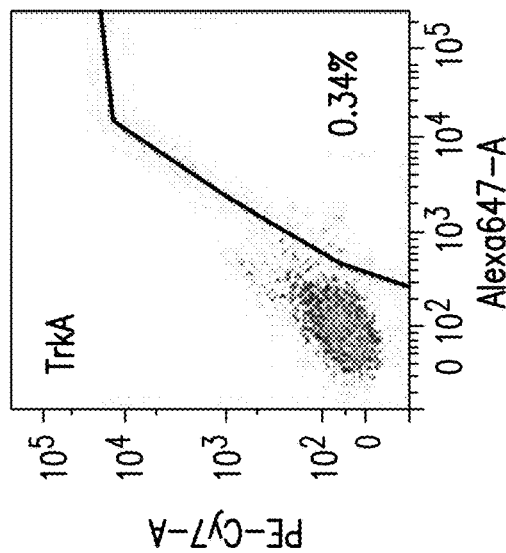
Figure 1D:
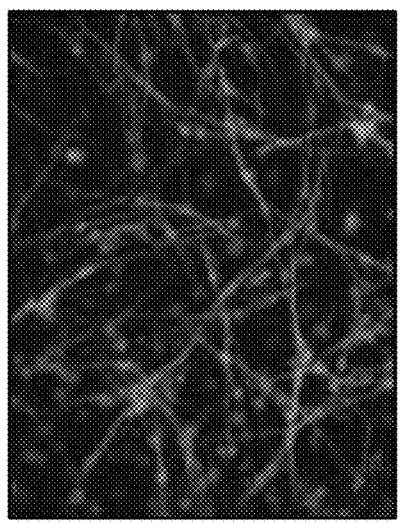

To induce neural differentiation, cells were plated on matrigel coated dishes and differentiations were induced once 100% confluency was reached, typically 24 hours after plating using Knockout Serum Replacement (KSR) media containing 820 ml of Knockout DMEM, 150 ml Knockout Serum Replacement, 1 mM L-glutamine, 100 µM MEM non-essential amino acids, and 0.1 mM β-mercaptoethanol. To inhibit SMAD signaling, 100 nM LDN-193189 and 10 µM SB431542 were added from day 0 through day 11. See FIG. 1A. Cells were fed every other day (i.e., 6 feedings with inhibitors, Day 0, Day 2, Day 4, Day 6, Day 8, and Day 10), and N2 media was added to the initial medium in increasing 25% increments every other day starting on day 4 (up to 100% N2 on day 10). Proprioceptor induction was initiated by the addition of 1.5 µM CHIR99021, 10 µM SU5402, and 10 µM DAPT daily from days 2 through day 11. On day 13, the cells were detached using accutase and washed twice in 1×PBS. Half of the cells were stained with TrkA (R&D systems, Minneapolis, USA), TrkB (R&D systems, Minneapolis, USA), TrkC (R&D systems, Minneapolis, USA) antibodies in DMEM/F12 media supplemented with 5% FBS and FACS analyzed (FIG. 1B). At this time point 10% of the cells expressed TrkC, a marker for proprioceptor neurons. The other half of the cells were replated onto polyornithin/laminin/fibronectin coated 96-wells at 280,000 cells per well in N2 differentiation media supplemented with 50×B-27 supplement (Life technologies), 20 ng/ml BDNF (R&D Systems), 20 ng/ml GDNF (PreproTech), 25 ng/ml β-NGF (PreproTech), 100 µg/ml Primocin (InvivoGen) and 10 µM Y-27632 (Tocris). The cells were fed every 2 to 3 days with N2 differentiation media supplemented with 50×B-27 supplement (Life technologies), 20 ng/ml BDNF (R&D Systems), 20 ng/ml GDNF (PreproTech), 25 ng/ml β-NGF (PreproTech), 100 µg/ml Primocin (InvivoGen). On day 20, they were detached using accutase, stained for TrkA, TrkB, TrkC and FACS analyzed as described above (FIG. 1C). At this time point, up to 80% of the cells expressed the proprioceptor marker TrkC (FIG. 1C). For replating and staining, cells positive for all three markers were FACS isolated and plated down onto polyornithin/laminin/fibronectin coated 96-wells at 280,000 cells per well in N2 differentiation media supplemented with 50×B-27 supplement (Life technologies), 20 ng/ml BDNF (R&D Systems), 20 ng/ml GDNF (PreproTech), 25 ng/ml β-NGF (PreproTech), 100 µg/ml Primocin (InvivoGen) and 10 µM Y-27632 (Tocris). 24 hours later, the cells were fixed in 4% paraformaldehyde for 20 minutes at room temperature, washed twice in 1×PBS and stained for BRN3A (mIgG1, 1:100, Millipore), TUJ1 (rabbit, 1:1000, Covance and DAPI (1:1000, Sigma-Aldrich) (FIG. 1D). Almost all TUJ1-positive neurons expressed the pan-sensory neuron marker BRN3A at this point.

Example 2—Cell Culturing Methods for Inducing Proprioceptors from Stem Cells

Figure 2A:
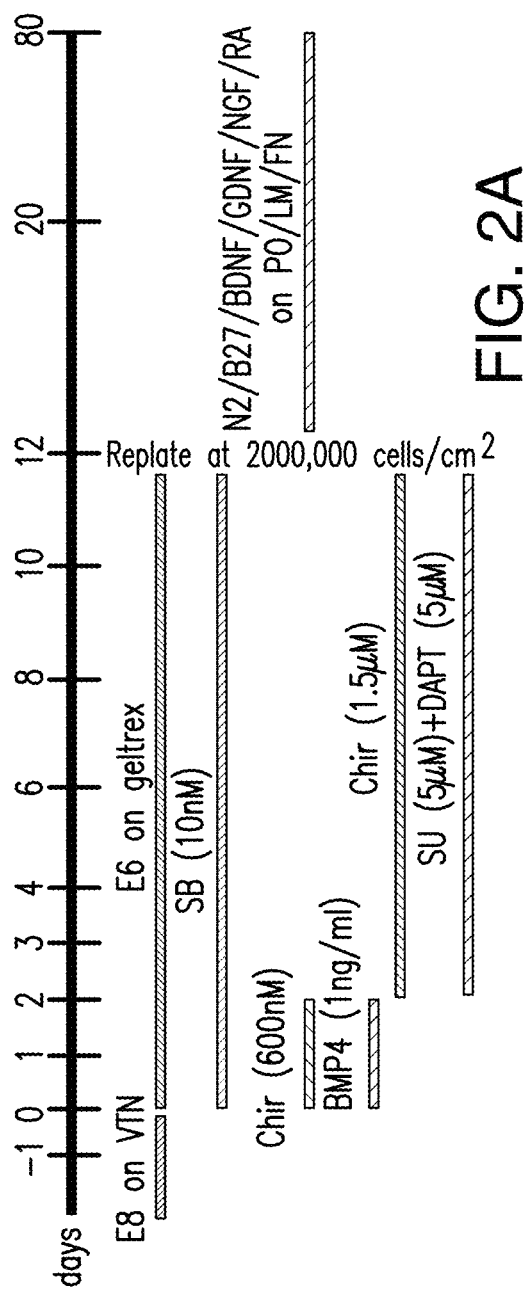
FIGS. 2A-2C. Induction of proprioceptors from human stem cells by an E8/E6 medium. (A) Schematic representation of the differentiation protocol. (B) Expression of CD49d of the cells on days 4, 8, 12, and 16. (C) Immunohistochemistry at day 16 and day 20.
Figure 2B:
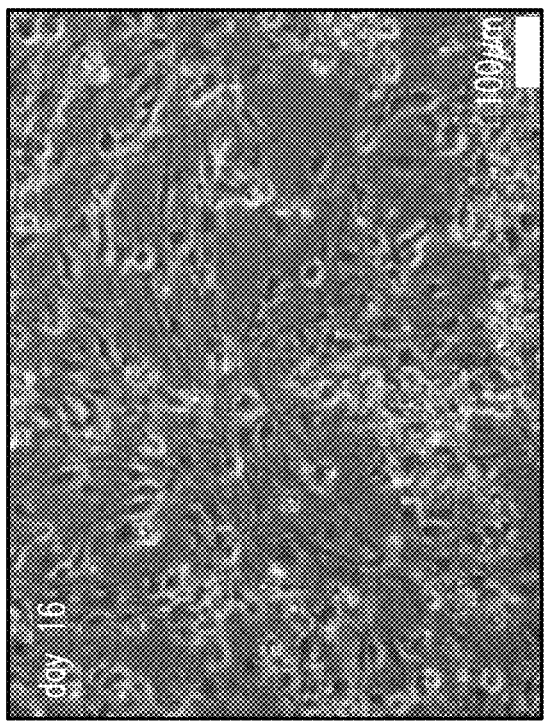
Figure 2B:
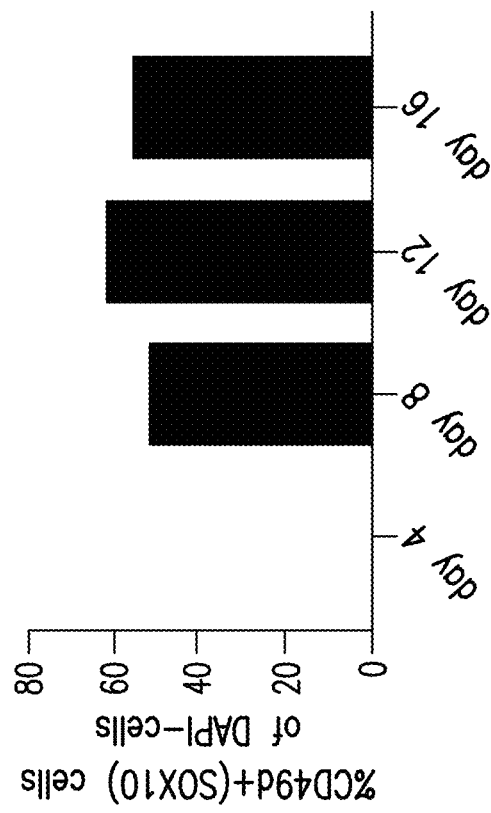
Figure 2C:
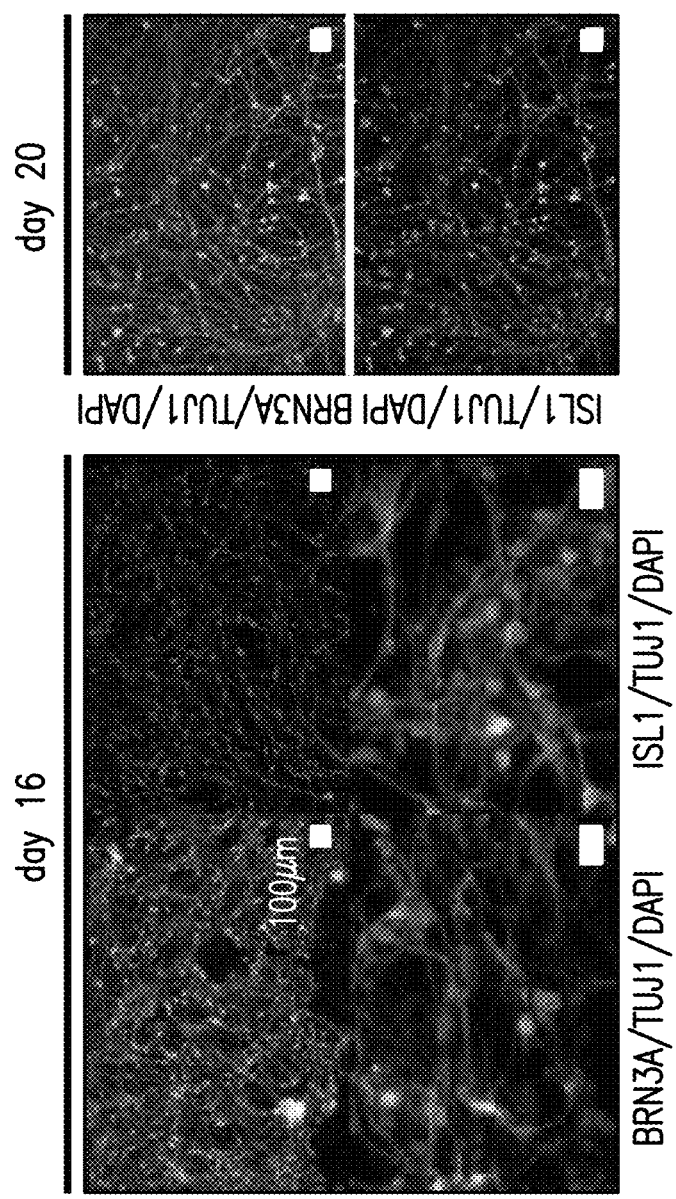

An E8/E6 medium was used to differentiate human stem cells into sensory neurons, including nociceptors, proprioceptors, and mechanoceptors. As shown in FIG. 2A, 600 nM CHIR99021 and 1 mg/mL BMP4 were added daily to the E8/E6 medium on day 0 and day 1, 10 nM SB was added daily to the E8/E6 medium from day 0 through day 12, 1.5 µM CHIR99021, 5 µM SU and 5 µM DAPT were added daily to the E8/E6 medium from day 2 through day 12. On day 4, day 8, day 12, and day 16, the cells were measured for CD49d expression. As shown in FIG. 2B, sensory neurons were derived from SOX10-positive neural crest lineage. On day 16 and day 20, cells were stained for BRN3A, TUJ1, and DAPI. As shown in FIG. 2C, majority of the cells at day 16 and day 20 had a peripheral sensory neuron character.

Figure 3A:
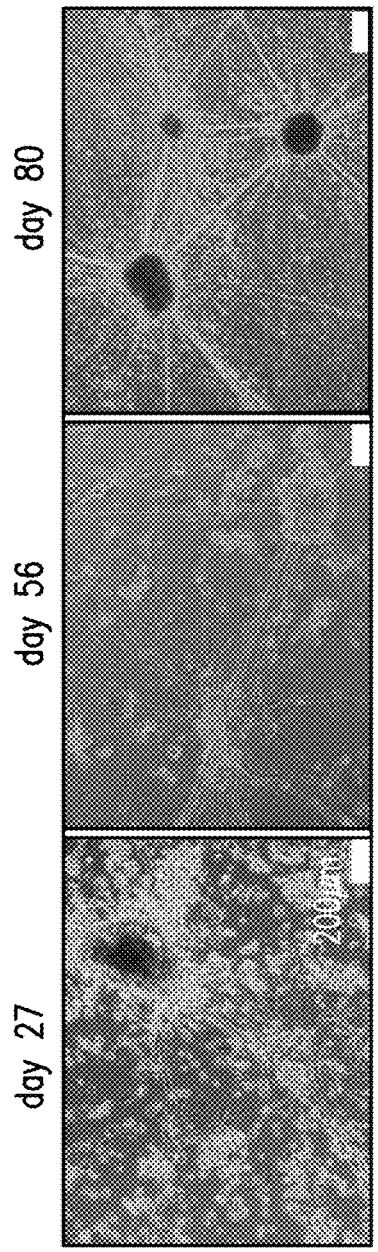
FIGS. 3A-3B. Generation of three sensory neuron subtypes. (A) Morphology of sensory neurons over time. (B) Percentage of three sensory neuron subtypes generated with different concentrations of Wnt-activation (CHIR99021).

Morphology of the generated sensory neurons at day 27, day 56 and day 80 was studied and the results are shown in FIG. 3A. As shown in FIG. 3A, the cells tended to cluster together the send thick axon bundles out, reminiscent of the typical ganglionic morphology of peripheral sensory neurons.

Figure 3B:
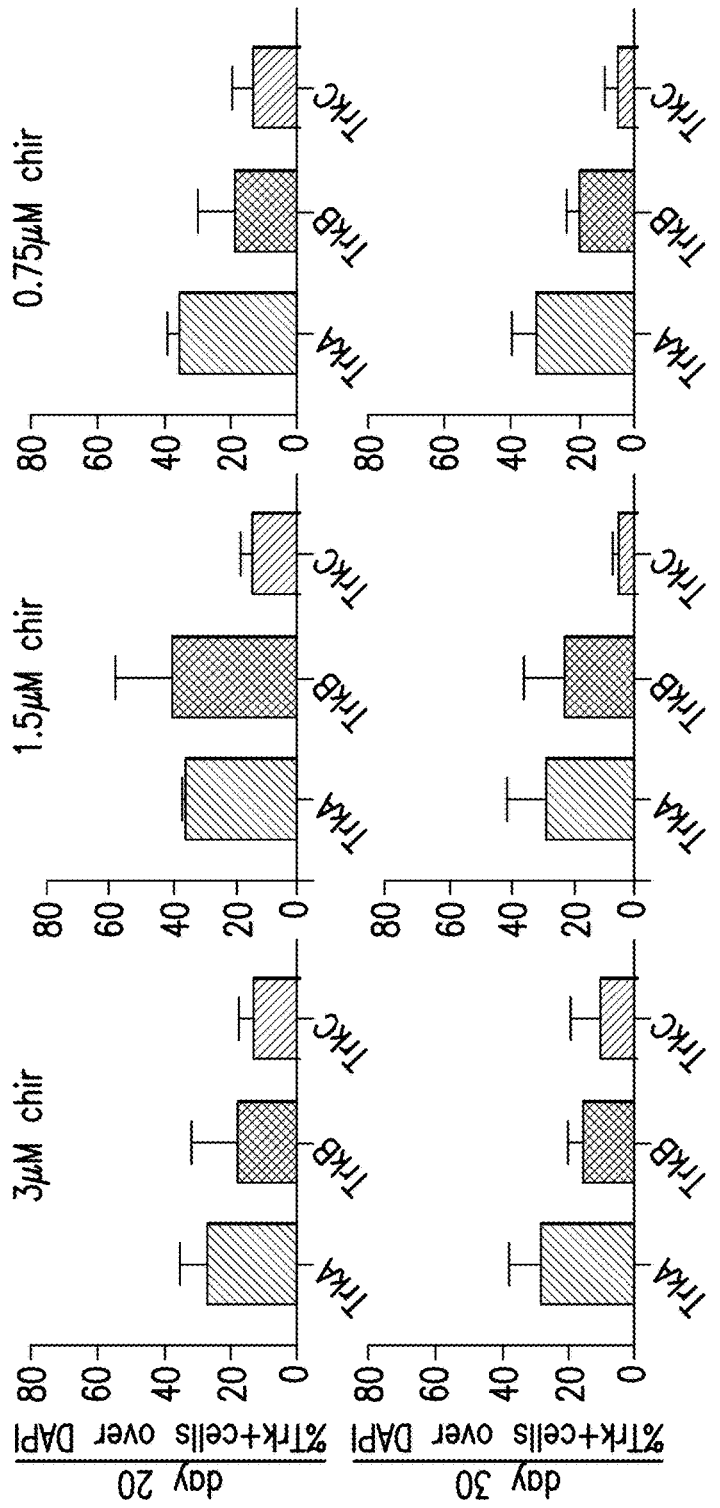

Next, different concentrations of CHIR99021 from day 2 through day 12 were tested, i.e., 3 µM, 1.5 µM, and 0.75 µM. TrkA is a nociceptor marker, TrkB is a mechanoreceptor marker, and TrkC is a proprioceptor marker. As shown in FIG. 3B, each of the three sensory neuron subtypes (nociceptors, proprioceptors, mechanoreceptors) were generated at similar efficiencies, regarding the concentration of CHIR99021 from day 2 through day 12.

Various patents and other publications are cited herein, the contents of which are hereby incorporated by reference in their entireties.

What is claimed is:

1. An in vitro method for inducing differentiation of human pluripotent stem cells to proprioceptors, comprising contacting stem cells with a transforming growth factor beta (TGFβ) receptor inhibitor, a bone morphogenetic protein (BMP), and a wingless (Wnt) activator to produce a population of proprioceptors, wherein
    (a) the contact of the cells with the BMP is for up to 2 days,
    (b) the contact of the cells with the TGFβ receptor inhibitor is for at least 12 days,
    (c) the contact of the cells with the Wnt activator is for at least 10 days;
    (d) the concentration of the Wnt activator is from 0.1 µM to 2.5 µM, and
    (e) the initial contact of the cells with the Wnt activator is within a four-day period from the initial contact of the cells with the TGFβ receptor inhibitor.

2. The method of claim 1, wherein the initial contact of the cells with the Wnt activator is on the same day as the initial contact of the cells with the TGFβ receptor inhibitor.

3. The method of claim 1, wherein the initial contact of the cells with the BMP is on the same day as the initial contact of the cells with the of TGFβ receptor inhibitor.

4. The method of claim 1, wherein the concentration of the BMP is up to 2 ng/mL.

5. The method of claim 1, wherein the initial contact of the cells with the Wnt activator is between 1 day and 4 days, or 2 days from the initial contact of the cells with the TGFβ receptor inhibitor.

6. The method of claim 1, comprising contacting the cells with the Wnt activator in a concentration of 1.5 µM, or less than 1.0 µM.

7. The method of claim 1, further comprising contacting the cells with an anaplastic lymphoma kinase (ALK) inhibitor.

8. The method of claim 7, wherein the initial contact of the cells with the ALK inhibitor is on the same day as the initial contact of the stem cells with the TGFβ receptor inhibitor.

9. The method of claim 7, wherein the ALK inhibitor comprises LDN193189.

10. The method of claim 1, further comprising contacting the cells with a fibroblast growth factor receptor (FGFR) inhibitor.

11. The method of claim 10, wherein the FGFR inhibitor is selected from the group consisting of SU5402, PD-161570, PD-173074, and mixtures thereof.

12. The method of claim 1, further comprising contacting the cells with a γ-secretase inhibitor.

13. The method of claim 12, wherein the γ-secretase inhibitor is selected from the group consisting of N4N-(3, 5-difluorophenacetyl-L-alanyl)]-(S)-phenylglycine t-butyl ester (DAPT), DAP-BpB, and mixtures thereof.

14. The method of claim 1, comprising:
    (a) contacting the cells with the TGFβ receptor inhibitor and an ALK inhibitor from day 0 through day 11, and contacting the cells with the Wnt activator, an FGFR inhibitor, and a γ-secretase inhibitor from day 2 through day 11; or
    (b) contacting cells with TGFβ receptor inhibitor and the Wnt activator from day 0 through day 12, contacting the cells with the BMP from day 0 through day 1, and contacting the cells with the FGFR inhibitor and the γ-secretase inhibitor from day 2 through day 12.

15. The method of claim 1, wherein the TGFβ receptor inhibitor comprises SB431542, and/or the Wnt activator is a glycogen synthase kinase 3β(GSK3β) inhibitor.

16. The method of claim 1, wherein the Wnt activator is CHIR99021.

17. The method of claim 1, wherein the human pluripotent stem cells are selected from the group consisting of human embryonic stem cells, human induced pluripotent stem cells, epiblast stem cells, and F-class pluripotent stem cells.

18. The method of claim 1, wherein the proprioceptors express at least one proprioceptor marker selected from the group consisting of TrkC, Runx3, CDHL1, ETV1, and ETV4, and combinations thereof.

19. The method of claim 1, wherein the BMP is selected from the group consisting of BMP2, BMP4, BMP6, and BMP7.

20. An in vitro method for inducing differentiation of human pluripotent stem cells to proprioceptors, comprising contacting stem cells with a transforming growth factor beta (TGFβ) receptor inhibitor, a bone morphogenetic protein (BMP), and a wingless (Wnt) activator to produce a population of proprioceptors, wherein
  (a) the contact of the cells with the BMP is for up to 2 days,
  (b) the contact of the cells with the TGFβ receptor inhibitor is for at least 12 days,
  (c) the contact of the cells with the Wnt activator is for at least 10 days; and
  (d) the concentration of the Wnt activator is from 0.1 µM to 2.5 µM.

* * * * *